(12) United States Patent
Tzeng et al.

(10) Patent No.: US 8,952,033 B2
(45) Date of Patent: Feb. 10, 2015

(54) 4-ANILINOFURO[2,3-B]QUINOLINE DERIVATIVES, THEIR PREPARATION PROCESSES, AND PHARMACEUTICAL COMPOSITIONS COMPRISING THE SAME

(75) Inventors: Cherng-Chyi Tzeng, Kaohsiung (TW); Yeh-Long Chen, Kaohsiung (TW); Yu-Wen Chen, Taipei (TW); Pei-Jung Lu, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 267 days.

(21) Appl. No.: 13/341,330

(22) Filed: Dec. 30, 2011

(65) Prior Publication Data
US 2013/0172336 A1 Jul. 4, 2013

(51) Int. Cl.
*C07D 491/048* (2006.01)
*A61K 31/4355* (2006.01)

(52) U.S. Cl.
CPC ........ *C07D 491/048* (2013.01); *A61K 31/4355* (2013.01)
USPC ........... 514/291; 514/232.8; 546/89; 544/126

(58) Field of Classification Search
CPC .................... C07D 491/048; A61K 31/4355
USPC .................. 546/89; 544/126; 514/291, 232.8
See application file for complete search history.

(56) References Cited

U.S. PATENT DOCUMENTS

| 4,943,579 A * | 7/1990 | Vishnuvajjala et al. ...... 514/283 |
| 6,750,223 B2 * | 6/2004 | Tzeng ............................ 514/291 |
| 2009/0325996 A1 * | 12/2009 | Lu et al. ........................ 514/283 |

OTHER PUBLICATIONS

Synthesis and Cytotoxic Evaluation of some 4-Anilinofuro[2,3-b]quinoline deravatives, I-Li Chen et al 2002.*
Synthesis and Anti-inflammatory evaluation of 4-anilinofuro[2,3b]quinoline and 4-phenoxyfuro[2,3-b]quinoline derivatives. Part 3, Yeh-Long Chen et al. 2004.*

* cited by examiner

*Primary Examiner* — Rita Desai
(74) *Attorney, Agent, or Firm* — Robert J. Sacco, Esq.; Fox Rothschild LLP

(57) ABSTRACT

Disclosed herein are novel 4-anilinofuro[2,3-b]quinoline derivatives of formula (I):

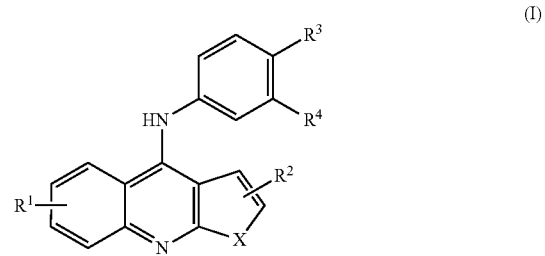

or a pharmaceutically acceptable salt thereof,
wherein each of the substituents is given the definition as set forth in the Specification and Claims.
Also disclosed are the preparation processes of these derivatives and their uses in the manufacture of pharmaceutical compositions and in the treatment of cancers.

12 Claims, 3 Drawing Sheets

4-ANILINOFURO[2,3-B]QUINOLINE DERIVATIVES, THEIR PREPARATION PROCESSES, AND PHARMACEUTICAL COMPOSITIONS COMPRISING THE SAME

BACKGROUND OF THE INVENTION

1. Field of the Invention

This invention relates to novel 4-anilinofuro[2,3-b]quinoline derivatives, which exhibit a broad and potent anticancer activity and improved solubility in water and oral bioavailability. This invention also relates to processes for preparing these derivatives, as well as the uses of the same in the manufacture of pharmaceutical compositions and in the treatment of cancers.

2. Description of the Related Art

Acridine derivatives are compounds having an acridine moiety, which is a planar tricyclic structure. The acridine derivatives are able to inhibit topoisomerase II by intercalating the acridine moiety thereof into DNA, thereby being capable of blocking DNA replication and transcription. Accordingly, the acridine derivatives, especially 9-anilinoacridine derivatives, have been extensively studied as potential chemotherapeutic agents (Denny W. A. et al. (1987), *J. Med. Chem.*, 30:658-663; Gamage S. A. et al. (1994), *J. Med. Chem.*, 37:1486-1494; and Gamage S. A. et al. (1997), *J. Med. Chem.*, 40:2634-2642).

In order to develop a new potent anticancer drug, the applicants synthesized a series of 4-anilinofuro[2,3-b]quinoline derivatives by replacing a benzene ring of the acridine moiety of 9-anilinoacridine with a furan ring (U.S. Pat. No. 6,750,223 B2; Chen I. L. et al. (2002), *Helv. Chem. Acta.*, 85:2214-2221; Zhao Y. L. et al. (2005), *Chem. Biodiver.*, 2:205-214: Chen Y. L. et al. (2005), *J. Med. Chem.*, 40:928-934; and Chen Y. L. et al., (2008), *Chem. Biodiver.*, 4:267-278). The thus obtained 4-anilinofuro[2,3-b]quinoline derivatives are structurally related to the 9-anilinoacridine derivatives.

Among the aforesaid 4-anilinofuro[2,3-b]quinoline derivatives synthesized by the applicants, 1-(4-(furo[2,3-b]quinolin-4-ylamino)phenyl)ethanone (referred to as compound 1 hereinafter) was verified to have an antiproliferative potency higher than that of amsacrine (m-AMSA), which is a 9-anilinoacridine derivative clinically used for treatment of leukemia and lymphoma, in an in vitro anticancer assay.

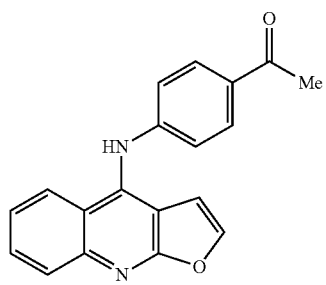

1-(4-(furo[2,3-b]quinolin-4-ylamino)phenyl)ethanone

In addition, (E)-1-(4-(furo[2,3-b]quinolin-4-ylamino)phenyl)ethanone oxime (a hydroxyimino derivative of compound 1, referred to as compound 2 hereinafter) and (E)-1-(4-(furo[2,3-b]quinolin-4-ylamino)phenyl)ethanone O-methyloxime (a methoxyimino derivative of compound 1, referred to as compound 3 hereinafter) were also shown to have an antiproliferative potency comparable to that of amsacrine. The applicants even further found that compound 1 is able to induce mitotic arrest and apoptosis by binding to tubulin and inhibiting tubulin polymerization (Huang Y. T. et al. (2005), *J. Med. Chem.*, 280:2771-2779).

Even though compounds 1, 2, 3 have a satisfactory antiproliferative potency, the same exhibit some drawbacks, such as low solubility in water, poor oral bioavailability, etc.

Low solubility in water is an intrinsic property possessed by numerous natural and synthetic drug candidates, and is normally associated with poor absorption and bioavailability. Indeed, low solubility in water and poor oral bioavailability are common problems found in drug development, particularly in anticancer drug development. Researchers hence endeavor to develop an anticancer drug that has satisfactory solubility in water and oral bioavailability. For instance, aminoalkyl functionality can be introduced into camptothecin having an anticancer activity so as to form a more highly water-soluble camptothecin derivative (e.g., topotecan and irinotecan), and a phosphate group can be attached to combretastatin A-4 (CA-4) having an anticancer activity so as to form more highly water-soluble combretastatin A-4 phosphate (CA-4P).

The applicants have attempted to improve solubility in water and oral bioavailability of 4-anilinofuro[2,3-b]quinoline derivatives by introducing thereinto an aminoalkyl side chain, and have proven that 4-anilinofuro[2,3-b]quinoline derivatives bearing an aminoalkyl side chain have enhanced solubility in water and oral bioavailability.

SUMMARY OF THE INVENTION

Therefore, according to a first aspect, this invention provides a compound of formula (I):

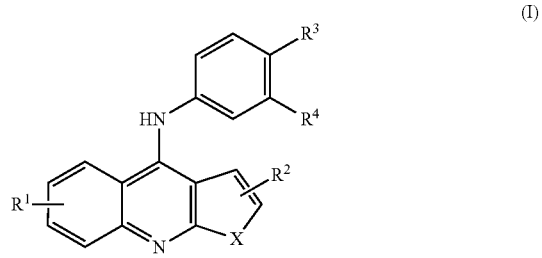

(I)

or a pharmaceutically acceptable salt thereof,
wherein:
X represents S, O, or NH;
$R^1$ and $R^2$, which may be the same or different, independently represent: H, halogen, a $C_1$-$C_4$ alkyl group, a hydroxyl group, a $C_1$-$C_4$ alkoxy group, a nitro group, or an amino group; and
one of $R^3$ and $R^4$ is H, and the other is

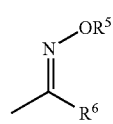

wherein $R^5$ is a $C_2$-$C_8$ aminoalkyl group, and $R^6$ represents H or a $C_1$-$C_4$ alkyl group.

In a second aspect, this invention provides a process for preparing the compound of formula (I) described above, which comprises subjecting a compound of formula (A):

  (A)

wherein $R^5$ has the same definition as that defined for the compound of formula (I) described above, to a reaction with a compound of formula (B):

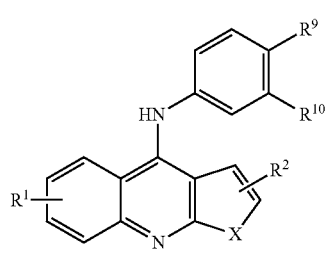  (B)

wherein $R^1$, $R^2$, and X have the same definitions as those defined for the compound of formula (I) described above; and one of $R^9$ and $R^{19}$ is H, and the other is

wherein $R^6$ has the same definition as that defined for the compound of formula (I) described above.

In a third aspect, this invention provides a pharmaceutical composition comprising the compound of formula (I) or the pharmaceutically acceptable salt thereof as described above.

In a fourth aspect, this invention provides a method of treating a subject having or suspected of having a cancer disease, which comprises administering to the subject the compound of formula (I) or the pharmaceutically acceptable salt thereof as described above.

BRIEF DESCRIPTION OF THE DRAWINGS

The above and other objects, features and advantages of this invention will become apparent with reference to the following detailed description and the preferred embodiments taken in conjunction with the accompanying drawing, in which.

DETAILED DESCRIPTION OF THE INVENTION

Figure 1:
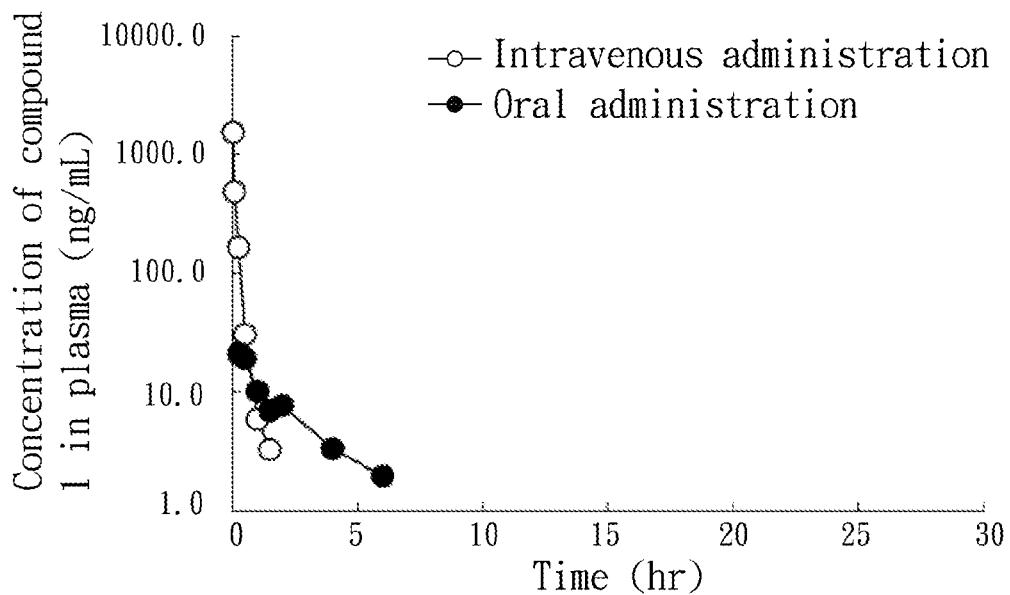
FIG. 1 shows the concentration of compound 1 in plasma at different time points after the intravenous administration or the oral administration of compound 1 to CD-1 mice.

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless defined otherwise, all technical and scientific terms used herein have the meaning commonly understood by a person skilled in the art to which this invention belongs. One skilled in the art will recognize many methods and materials similar or equivalent to those described herein, which could be used in the practice of the present invention. Indeed, the present invention is in no way limited to the methods and materials described. For clarity, the following definitions are used herein.

In a previous study, the applicants synthesized a series of 4-anilinofuro[2,3-b]quinoline derivatives, and tested the same to determine anticancer activity thereof. Among the 4-anilinofuro[2,3-b]quinoline derivatives synthesized by the applicants, compounds 1, 2, 3 as mentioned in the section of "Description of the Related Art" have the ability to inhibit growth of a variety of tumor/cancer cells such as non-small cell lung cancer cells, breast cancer cells, central nervous system cancer cells, leukemia cells, colon cancer cells, melanoma cells, ovarian cancer cells, renal cancer cells, and prostate cancer cells. Even though compounds 1, 2, 3 have satisfactory antiproliferative potency, the same have drawbacks like low solubility in water, poor oral bioavailability, etc.

The applicants strived to overcome the aforementioned drawbacks by virtue of experiments, and found that introduction of an aminoalkyl group to an oxime moiety of a 4-anilinofuro[2,3-b]quinoline derivative can improve solubility in water and oral bioavailability.

Accordingly, this invention provides a compound of formula (I):

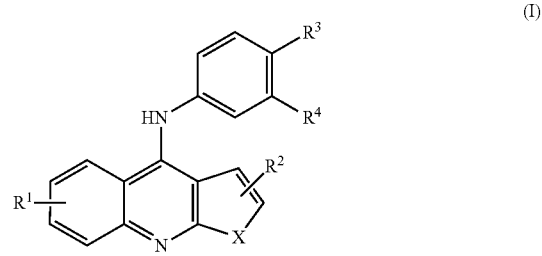  (I)

or a pharmaceutically acceptable salt thereof, wherein:

X represents S, O, or NH;

$R^1$ and $R^2$, which may be the same or different, independently represent: H, halogen, a $C_1$-$C_4$ alkyl group, a hydroxyl group, a $C_1$-$C_4$ alkoxy group, a nitro group, or an amino group; and one of $R^3$ and $R^4$ is H, and the other is

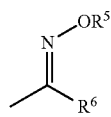

wherein $R^5$ is a $C_2$-$C_8$ aminoalkyl group, and $R^6$ represents H or a $C_1$-$C_4$ alkyl group.

The term "halogen" as used herein refers to fluorine, chlorine, bromine or iodine.

The term "alkyl group" as used herein alone or as part of another group refers to a straight or branched saturated monovalent hydrocarbon group. The term "alkyl group" as used herein alone or as part of another group includes, but is not limited to, methyl, ethyl, propyl, isopropyl, n-butyl, isobutyl, sec-butyl, tert-butyl, n-pentyl, isopentyl, neopentyl, n-hexyl, isohexyl, heptyl, isoheptyl, octyl, the various branched chain isomers thereof, etc.

The term "alkoxy group" as used herein refers to a group of formula —OR', wherein R' is an alkyl group. The term "alkoxy group" as used herein includes, but is not limited to, methoxy, ethoxy, n-propoxy, isopropoxy, n-butoxy, isobutoxy, sec-butoxy, tert-butoxy, etc. In a preferred embodiment of this invention, the alkoxy group is a methoxy group.

The term "aminoalkyl group" as used herein refers to an alkyl group substituted with at least one amino group, wherein the amino group may be a primary amine, a secondary amine, or a tertiary amine. In a preferred embodiment of this invention, the aminoalkyl group is a $C_2$-$C_4$ aminoalkyl group. In a more preferred embodiment of this invention, the aminoalkyl group is an aminoethyl group.

Preferred compounds of formula (I) according to this invention include compounds of formula (II):

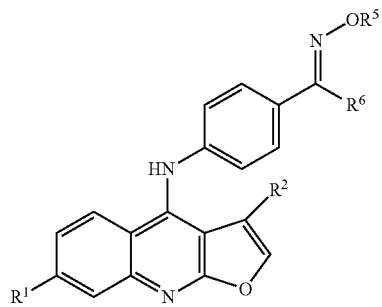

(II)

wherein:
$R^1$ represents H or a $C_1$-$C_4$ alkoxy group;
$R^2$ represents H or halogen;
$R^5$ is a $C_2$-$C_8$ aminoalkyl group; and
$R^6$ is a $C_1$-$C_4$ alkyl group.
Preferably, $R^5$ is:

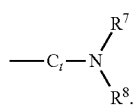

In a preferred embodiment, $R^7$ and $R^8$, which may be the same or different, independently represent H or an alkyl group, and t is an integer from 2 to 4. In another preferred embodiment, $R^7$ and $R^8$ together with the nitrogen atom to which $R^7$ and $R^8$ are attached form a 5- to 6-membered heterocyclic ring, and t is an integer from 2 to 4. $R^7$ and $R^8$ together with the nitrogen atom to which $R^7$ and $R^8$ are attached may form a 6-membered heterocyclic ring that has an oxygen atom.

Representative examples of $R^5$ are:

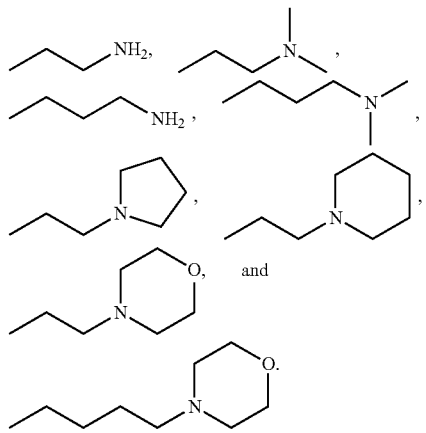

Representative examples of compounds of formula (I) according to this invention include, but are not limited to:
(E)-1-(4-(furo[2,3-b]quinolin-4-ylamino)phenyl)ethanone O-2-aminoethyl oxime;
(E)-1-(4-(furo[2,3-b]quinolin-4-ylamino)phenyl)ethanone O-2-(dimethylamino)ethyl oxime;
(E)-1-(4-(furo[2,3-b]quinolin-4-ylamino)phenyl)ethanone O-3-aminopropyl oxime;
(E)-1-(4-(furo[2,3-b]quinolin-4-ylamino)phenyl)ethanone O-3-(dimethylamino)propyl oxime;
(E)-1-(4-(furo[2,3-b]quinolin-4-ylamino)phenyl)ethanone O-2-(pyrrolidin-1-yl)ethyl oxime;
(E)-1-(4-(furo[2,3-b]quinolin-4-ylamino)phenyl)ethanone O-2-(piperidin-1-yl)ethyl oxime;
(E)-1-(4-(furo[2,3-b]quinolin-4-ylamino)phenyl)ethanone O-2-morpholinoethyl oxime;
(E)-1-(4-(furo[2,3-b]quinolin-4-ylamino)phenyl)ethanone O-4-morpholinobutyl oxime;
(E)-1-(4-(3-chlorofuro[2,3-b]quinolin-4-ylamino)phenyl) ethanone O-2-aminoethyl oxime;
(E)-1-(4-(3-chlorofuro[2,3-b]quinolin-4-ylamino)phenyl) ethanone O-2-(dimethylamino)ethyl oxime;
(E)-1-(4-(3-chlorofuro[2,3-b]quinolin-4-ylamino)phenyl) ethanone O-3-aminopropyl oxime;
(E)-1-(4-(3-chlorofuro[2,3-b]quinolin-4-ylamino)phenyl) ethanone O-3-(dimethylamino)propyl oxime;
(E)-1-(4-(3-chlorofuro[2,3-b]quinolin-4-ylamino)phenyl) ethanone O-2-(pyrrolidin-1-yl)ethyl oxime;
(E)-1-(4-(3-chlorofuro[2,3-b]quinolin-4-ylamino)phenyl) ethanone O-2-(piperidin-1-yl)ethyl oxime;
(E)-1-(4-(3-chlorofuro[2,3-b]quinolin-4-ylamino)phenyl) ethanone O-2-morpholinoethyl oxime;
(E)-1-(4-(3-chlorofuro[2,3-b]quinolin-4-ylamino)phenyl) ethanone O-4-morpholinobutyl oxime;
(E)-1-(4-(7-methoxyfuro[2,3-t]quinolin-4-ylamino)phenyl) ethanone O-2-aminoethyl oxime;
(E)-1-(4-(7-methoxyfuro[2,3-b]quinolin-4-ylamino)phenyl) ethanone O-2-(dimethylamino)ethyl oxime;
(E)-1-(4-(7-methoxyfuro[2,3-b]quinolin-4-ylamino)phenyl) ethanone O-3-aminopropyl oxime;

(E)-1-(4-(7-methoxyfuro[2,3-b]quinolin-4-ylamino)phenyl) ethanone O-3-(dimethylamino)propyl oxime;

(E)-1-(4-(7-methoxyfuro[2,3-b]quinolin-4-ylamino)phenyl) ethanone O-2-(pyrrolidin-1-yl)ethyl oxime;

(E)-1-(4-(7-methoxyfuro[2,3-b]quinolin-4-ylamino)phenyl) ethanone O-2-(piperidin-1-yl)ethyl oxime;

(E)-1-(4-(7-methoxyfuro[2,3-b]quinolin-4-ylamino)phenyl) ethanone O-2-morpholinoethyl oxime;

(E)-1-(4-(7-methoxyfuro[2,3-b]quinolin-4-ylamino)phenyl) ethanone O-4-morpholinobutyl oxime;

(E)-1-(4-(3-chloro-7-methoxyfuro[2,3-b]quinolin-4-ylamino)phenyl)ethanone O-2-aminoethyl oxime;

(E)-1-(4-(3-chloro-7-methoxyfuro[2,3-b]quinolin-4-ylamino)phenyl)ethanone O-2-(dimethylamino)ethyl oxime;

(E)-1-(4-(3-chloro-7-methoxyfuro[2,3-b]quinolin-4-ylamino)phenyl)ethanone O-3-aminopropyl oxime;

(E)-1-(4-(3-chloro-7-methoxyfuro[2,3-b]quinolin-4-ylamino)phenyl)ethanone O-3-(dimethylamino) propyl oxime;

(E)-1-(4-(3-chloro-7-methoxyfuro[2,3-b]quinolin-4-ylamino)phenyl)ethanone O-2-(pyrrolidin-1-yl)ethyl oxime;

(E)-1-(4-(3-chloro-7-methoxyfuro[2,3-b]quinolin-4-ylamino) phenyl)ethanone O-2-(piperidin-1-yl)ethyl oxime;

(E)-1-(4-(3-chloro-7-methoxyfuro[2,3-L]quinolin-4-ylamino)phenyl)ethanone O-2-morpholinoethyl oxime; and (E)-1-(4-(3-chloro-7-methoxyfuro[2,3-b]quinolin-4-ylamino)phenyl)ethanone O-4-morpholinobutyl oxime.

The compounds of formula (I) according to this invention may be in their free form or in the form of a pharmaceutically acceptable salt thereof. In addition, the compounds of formula (I) according to this invention may also exist as a stereoisomer or in the form of solvates represented by the hydrate. Therefore, it is contemplated that these stereoisomers and solvates fall within the technical concept of this invention.

As used herein, the pharmaceutically acceptable salt includes, but is not limited to: salts with inorganic acids, such as hydrochloride, hydrobromide, sulfate and phosphate; salts with organic acids, such as acetate, maleate, tartrate, and methanesulfonate; and salts with amino acids, such as arginine, aspartic acid and glutamic acid.

A representative example regarding the pharmaceutically acceptable salts of the compounds of formula (I) according to this invention is a hydrochloride salt of (E)-1-(4-(furo[2,3-b]quinolin-4-ylamino)phenyl)ethanone O-2-aminoethyl oxime.

This invention also provides a process for preparing the compound of formula (I) described above, which comprises subjecting a compound of formula (A):

wherein $R^5$ has the same definition as that defined for the compound of formula (I) described above, to a reaction with a compound of formula (B):

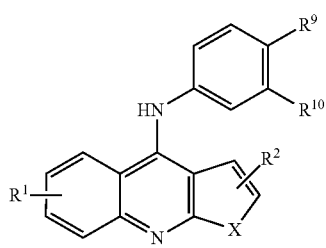

(B)

wherein $R^1$, $R^2$, and X have the same definitions as those defined for the compound of formula (I) described above; and one of $R^9$ and $R^{10}$ is H, and the other is

wherein $R^6$ has the same definition as that defined for the compound of formula (I) described above.

The compounds of formula (I) according to this invention have been proven to possess excellent activities against the growth of tumor/cancer cells, in particular breast cancer cells, human stomach adenocarcinoma cells, human prostate cancer cells, human cervical epithelioid carcinoma cells, human esophageal carcinoma cells, human lung adenocarcinoma cells, non-small cell lung carcinoma cells, renal cell carcinoma cells, hepatocellular carcinoma cells, human oral squamous-cell carcinoma cells, central nervous system carcinoma cells, and metastatic lung adenocarcinoma cells. It is thus contemplated that the compounds of formula (I) according to this invention or the pharmaceutically acceptable salts thereof can be used in the treatment of tumors or cancers in a subject, including human and other mammals.

Accordingly, this invention provides a method of treating a subject having or suspected of having a cancer disease, which comprises administering to the subject the compound of formula (I) or the pharmaceutically acceptable salt thereof as described above.

This invention also envisions the application of the compounds of formula (I) according to this invention, or the pharmaceutically acceptable salts thereof, in the manufacture of pharmaceutical compositions for use in tumor/cancer therapy. Therefore, this invention provides a pharmaceutical composition comprising the compound of formula (I) as described above, or the pharmaceutically acceptable salt thereof, for the treatment of tumors or cancers in a subject, including human and other mammals.

The pharmaceutical composition according to this invention can additionally comprise a pharmaceutically acceptable carrier widely employed in the art of drug-manufacturing. For instance, the pharmaceutically acceptable carrier may include one or more of the following agents: solvents, emulsifiers, suspending agents, decomposers, binding agents, excipients, stabilizing agents, chelating agents, diluents, gelling agents, preservatives, lubricants, disintegrating agents, absorption delaying agents, liposomes, and the like.

The pharmaceutical composition according to this invention may be administered parenterally or orally in a suitable pharmaceutical form. Suitable pharmaceutical forms include sterile aqueous solutions or dispersions, sterile powders, tablets, troches, pills, capsules, and the like.

EXAMPLES

The present invention will be described in more detail with reference to the following examples, which are given for the purpose of illustration only and are not intended to limit the scope of the present invention.

The compounds of formula (I) according to this invention can be prepared according to the following synthesis scheme and protocols.

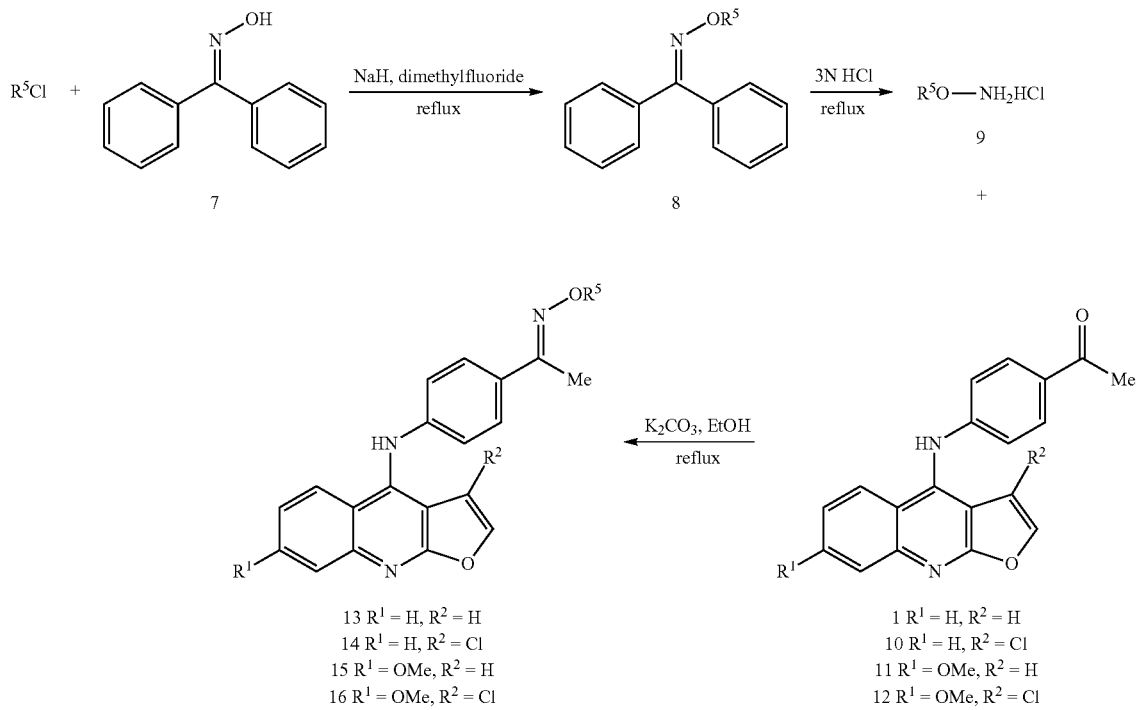

Scheme 1

As shown in Scheme 1, benzophenone oxime (compound 7) is subjected to an alkylation treatment using aminoalkyl chloride, thereby forming benzophenone aminoalkyloxime (compound 8). Compound 8 is hydrolyzed with 3N HCl such that a hydrochloride salt of aminoalkoxyamine (compound 9) is formed. A reaction of compound 9 with 1-(4-(furo[2,3-b]quinolin-4-ylamino)phenyl)ethanone (i.e., compound 1 as described above) yields compound 13. In addition, compound 9 can be subjected to a reaction with 1-(4-(3-chlorofuro[2,3-b]quinolin-4-ylamino)phenyl)ethanone (compound 10), 1-(4-(7-methoxyfuro[2,3-b]quinolin-4-ylamino)phenyl)ethanone (compound 11), or 1-(4-(3-chloro-7-methoxyfuro[2,3-b]quinolin-4-ylamino)phenyl)ethanone (compound 12), so as to correspondingly form compound 14, compound 15, or compound 16. It should be noted that compounds 13, 14, 15, 16 are not only the compounds of formula (I), but are also the compounds of formula (II).

Representative compounds of formula (I) according to this invention are shown in Table 1.

TABLE 1

Structures of representative compounds of formula (I) according to this invention.

| Compound | $R^1$ | $R^2$ | $R^5$ |
|---|---|---|---|
| 13a | H | H | ~~~NH$_2$ |
| 13b | H | H | ~~~N(Me)$_2$ |
| 13c | H | H | ~~~~NH$_2$ |
| 13d | H | H | ~~~~N(Me)$_2$ |
| 13e | H | H | ~~~-pyrrolidinyl |

TABLE 1-continued

Structures of representative compounds of formula (I) according to this invention.

| Compound | R¹ | R² | R⁵ |
|---|---|---|---|
| 13f | H | H | 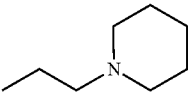 |
| 13g | H | H | 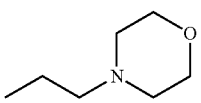 |
| 13h | H | H | 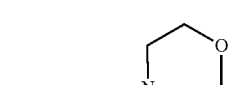 |
| 14a | H | Cl |  |
| 14b | H | Cl | 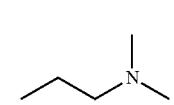 |
| 14c | H | Cl | 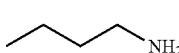 |
| 14d | H | Cl | 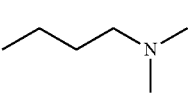 |
| 14e | H | Cl | 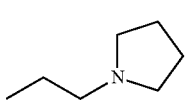 |
| 14f | H | Cl | 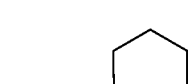 |
| 14g | H | Cl | 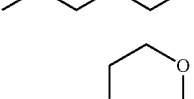 |
| 14h | H | Cl | 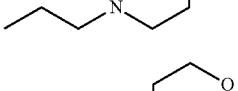 |
| 15a | —OMe | H | 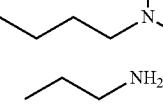 |
| 15b | —OMe | H | 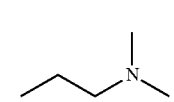 |
| 15c | —OMe | H | 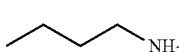 |
| 15d | —OMe | H | 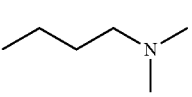 |
| 15e | —OMe | H | 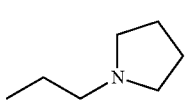 |
| 15f | —OMe | H | 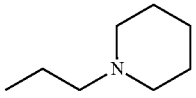 |
| 15g | —OMe | H | 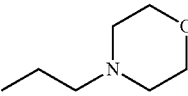 |
| 15h | —OMe | H | 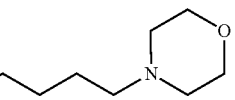 |
| 16a | —OMe | Cl | 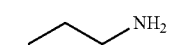 |
| 16b | —OMe | Cl | 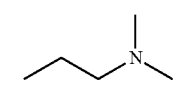 |
| 16c | —OMe | Cl |  |
| 16d | —OMe | Cl | 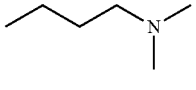 |
| 16e | —OMe | Cl | 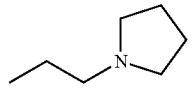 |
| 16f | —OMe | Cl | 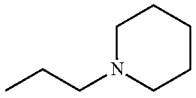 |
| 16g | —OMe | Cl | 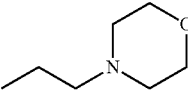 |
| 16h | —OMe | Cl | 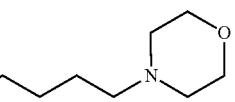 |

Note:
—OMe represents methoxy.

General Procedures:

The thin layer chromatography (TLC) was performed using pre-coated silica gel 60 $F_{254}$ plates (E. Merck & Co.), and was detected using a UV light at 254 nm.

The flash column chromatography was performed using Guderan Si 60 (particle size 0.040-0.063 mm, manufactured by E. Merck & Co.) as the solid phase in combination with a suitable eluent for separation and purification.

The melting point of each of the compounds synthesized in the following examples was measured by an uncorrected Electrothermal IA9100 digital melting-point apparatus.

IR spectra were obtained using a Perkin-Elmer System 2000 infrared spectrophotometer.

UV spectra were acquired using a Shimadzu UV-160A UV-VIS spectrophotometer and MeOH as a solvent, with maximum absorbance being represented by $\lambda_{max}$ in nm.

$^1$H-NMR and $^{13}$C-NMR spectra were obtained using a Varian Unity-400 (400 MHz) nuclear magnetic resonance spectrometer, with chemical shifts being represented by δ in ppm using TMS (0 ppm) as an internal standard, and coupling constants being represented by J in Hz.

Elemental analyses were carried out on a Heraeus CHN-O-Rapid elemental analyzer.

The high-resolution mass spectra (HRMS) were collected using a Bruker APEX II (ESI) mass spectrometer.

Synthesis Ex. 1

E)-1-(4-(Furo[2,3-b]quinolin-4-ylamino)phenyl) ethanone O-2-aminoethyl oxime (Compound 13a 1-(4-(furo[2,3-b]quinolin-4-ylamino)phenyl)ethanone (compound 1) was prepared according to the method as described in Example 4 of U.S. Pat. No. 6,750,223 B2. The thus obtained compound 1 (0.30 g, 1 mmol), 2-aminoethoxyamine.HCl (0.28 g, 2.5 mmol), and $K_2CO_3$ (0.69 g, 5.0 mmol) were added into EtOH (10 mL). The resultant mixture was subjected to reflux for 4 hours (TLC monitoring), followed by evaporation under reduced pressure. The residue thus acquired was dissolved in $CH_2Cl_2$ (50 mL). The $CH_2Cl_2$ layer was washed sequentially with $H_2O$ and brine, was dried using $Na_2SO_4$, and was subjected to an evaporation treatment. The resultant residue was purified via flash column chromatography ($MeOH/CH_2Cl_2$=1/50), followed by recrystallization from EtOH. The title compound 13a as a light yellow solid (0.45 g, 96% yield) was obtained.

Detected Properties of the Title Compound:
M.p.: 112-113° C. IR (KBr): 3216, 1578, 1517. UV (MeOH): 372 (4.22), 260 (4.52), 208 (4.53). $^1$H NMR (400 MHz, DMSO-$d_6$): 2.29 (s, 3H, $CH_3$), 3.17 (m, 2H, $OCH_2\underline{CH_2}N$), 4.35 (t, 2H, J=5.0 Hz, $O\underline{CH_2}CH_2N$), 5.94 (d, 1H, J=2.8 Hz, 3-H), 7.33-7.35 (m, 2H, ArH), 7.57-7.61 (m, 1H, 6-H), 7.78-7.88 (m, 4H, 2-, 7-H, ArH), 8.00 (d, 1H, J=8.0 Hz, 5-H), 8.23 (br s, 2H, $NH_2$), 8.60 (d, 1H, J=8.4 Hz, 8-H), 10.37 (br s, 1H, NH). $^{13}$C NMR (100 MHz, DMSO-$d_6$): 12.63, 38.27, 69.78, 103.86, 106.07, 117.21, 122.75 (2C), 123.76, 123.95, 125.02, 127.01 (2C), 130.81, 131.82, 141.60, 141.98, 143.07, 144.76, 155.14, 160.44. Anal. calc. for $C_{21}H_{20}N_4O_2$.0.6 $H_2O$.0.5HCl: C, 64.77; H, 5.62; N, 14.39. found: C, 64.88; H, 5.97; N, 14.17. HRMS (ESI): calc. for $C_{21}H_{21}N_4O_2$ $[M+H]^+$: 361.1664. found: 361.1663.

Hydrochloride Salt of the Title Compound:
Compound 13a (0.38 g) and 6 N HCl (2 mL) were added into EtOH (20 mL), followed by stirring at room temperature for 2 hours. The resultant precipitate was collected, and was recrystallized from EtOH to yield a hydrochloride salt of compound 13a. The elemental analysis data of the hydrochloride salt of compound 13a is as follows. Anal. calc. for $C_{21}H_{20}N_4O_2$.0.6 $H_2O$.1.8HCl: C, 57.74; H, 5.31; N, 12.83. found: C, 58.07; H, 5.71; N, 12.43.

Synthesis Ex. 2

(E)-1-(4-(Furo[2,3-b]quinolin-4-ylamino)phenyl) ethanone O-2-(dimethylamino)ethyl oxime (Compound 13b)

The title compound 13b was synthesized substantially according to the procedures as set forth in the above Synthesis Example 1, except that 2-dimethylaminoethoxyamine.HCl was used in place of 2-aminoethoxyamine.HCl, and that the recrystallization step is not required. The title compound 13b as a deep brown liquid (90% yield) was obtained.

Detected Properties of the Title Compound:
IR (KBr): 3221, 1578, 1519. UV (MeOH): 372 (4.18), 260 (4.48), 208 (4.50).
$^1$H NMR (400 MHz, CDCl$_3$): 2.27 (s, 3H, $CH_3$), 2.37 (s, 6H, $N(CH_3)_2$), 2.74 (t, 2H, J=5.8 Hz, $OCH_2\underline{CH_2}N$), 4.35 (t, 2H, J=5.8 Hz, $O\underline{CH_2}CH_2N$), 6.19 (d, 1H, J=2.8 Hz, 3-H), 6.90 (br s, 1H, NH), 7.15-7.17 (m, 2H, ArH), 7.47-7.52 (m, 2H, 2-H, 6-H), 7.67-7.74 (m, 3H, 7-H, ArH), 8.04 (dd, 1H, J=8.8, 1.2 Hz, 5-H), 8.09 (dd, 1H, J=8.8, 2.4 Hz, 8-H). $^{13}$C NMR (100 MHz, CDCl$_3$): 12.74, 45.91 (2C), 58.20, 72.29, 105.73, 106.09, 118.31, 120.61, 120.92 (2C), 123.86, 127.10 (2C), 129.21, 129.23, 132.12, 140.27, 141.68, 142.84, 145.99, 154.00, 163.28. Anal. calc. for $C_{23}H_{24}N_4O_2$.2.0 $H_2O$.1.1HCl: C, 59.46; H, 6.31; N, 12.06. found: C, 59.68; H, 6.40; N, 11.77. HRMS (ESI): calc. for $C_{23}H_{25}N_4O_2[M+H]^+$: 389.1977. found: 389.1979.

Synthesis Ex. 3

E)-1-(4-(Furo[2,3-b]quinolin-4-ylamino)phenyl) ethanone O-3-aminopropyl oxime (Compound 13c)

The title compound 13c was synthesized substantially according to the procedures as set forth in the above Synthesis Example 1, except that 3-aminopropoxyamine.HCl was used in place of 2-aminoethoxyamine.HCl. The title compound 13c as a light yellow solid (96% yield) was obtained.

Detected Properties of the Title Compound:
M.p.: 83-85° C. IR (KBr): 3237, 1578, 1517. UV (MeOH): 366 (4.20), 258 (4.48), 210 (4.50). $^1$H NMR (400 MHz, CDCl$_3$): 1.90 (quin, 2H, J=6.4 Hz, $OCH_2\underline{CH_2}CH_2N$), 2.25 (s, 3H, $CH_3$), 2.88 (t, 2H, J=6.8 Hz, $OCH_2CH_2\underline{CH_2}N$), 4.30 (t, 2H, J=6.0 Hz, $O\underline{CH_2}CH_2CH_2N$), 6.17 (d, 1H, J=2.8 Hz, 3-H), 7.03 (br s, 1H, NH), 7.14-7.17 (m, 2H, ArH), 7.46-7.50 (m, 2H, 2-H, 6-H), 7.66-7.73 (m, 3H, 7-H, ArH), 8.04-8.10 (m, 2H, 5-H, 8-H). $^{13}$C NMR (100 MHz, CDCl$_3$): 12.54, 33.25, 39.34, 72.01, 105.74, 106.01, 118.31, 120.69, 120.98 (2C), 123.79, 127.01 (2C), 129.16, 129.18, 132.14, 140.39, 141.67, 142.76, 145.97, 153.72, 163.27. Anal. calc. for $C_{22}H_{22}N_4O_2$.0.9 $H_2O$: C, 67.64; H, 6.14; N, 14.34. found: C, 67.97; H, 6.32; N, 14.02. HRMS (ESI): calc. for $C_{22}H_{23}N_4O_2$ $[M+H]^+$: 375.1821. found: 375.1823.

Synthesis Ex. 4

(E)-1-(4-(Furo[2,3-b]quinolin-4-ylamino)phenyl) ethanone O-3-(dimethylamino)propyl oxime (Compound 13d)

The title compound 13d was synthesized substantially according to the procedures as set forth in the above Synthesis Example 1, except that 3-dimethylaminopropoxyamine.HCl was used in place of 2-aminoethoxyamine.HCl. The title compound 13d as a yellow solid (75% yield) was obtained.

Detected Properties of the Title Compound:
M.p.: 83-85° C. IR (KBr): 3219, 1578, 1519. UV (MeOH): 368 (4.26), 258 (4.53), 210 (4.53). $^1$H NMR (400 MHz, CDCl$_3$): 1.99-2.06 (m, 2H, $OCH_2\underline{CH_2}CH_2N$), 2.25 (s, 3H, $CH_3$), 2.39 (s, 6H, $N(\underline{CH_3})_2$), 2.59 (t, 2H, J=7.6 Hz, $OCH_2CH_2\underline{CH_2}N$), 4.26 (t, 2H, J=6.2 Hz, $O\underline{CH_2}CH_2CH_2N$), 6.19 (d, 1H, J=2.8 Hz, 3-H), 6.93 (br s, 1H, NH), 7.14-7.17 (m, 2H, ArH), 7.47-7.52 (m, 2H, 2-H, 6-H), 7.67-7.74 (m, 3H, 7-H, ArH), 8.04-8.10 (m, 2H, 8-H, 5-H). $^{13}$C NMR (100 MHz, CDCl$_3$): 12.52, 26.93, 44.93 (2C), 56.34, 71.99, 105.74, 106.07, 118.34, 120.75, 120.96 (2C), 123.81, 127.03 (2C), 129.14, 129.19, 132.07, 140.40, 141.75, 142.77, 145.97, 153.92, 163.27. Anal. calc. for $C_{24}H_{26}N_4O_2$.0.5 $H_2O$:

C, 67.43; H, 6.39; N, 13.11. found: C, 67.35; H, 6.69; N, 12.94. HRMS (ESI): calc. for $C_{24}H_{27}N_4O_2$ $[M+H]^+$: 403.2134. found: 403.2136.

Synthesis Ex. 5

(E)-1-(4-(Furo[2,3-b]quinolin-4-ylamino)phenyl) ethanone O-2-(pyrrolidin-1-yl)ethyl oxime (Compound 13e)

The title compound 13e was synthesized substantially according to the procedures as set forth in the above Synthesis Example 1, except that 2-pyrrolidin-1-ylethoxyamine.HCl was used in place of 2-aminoethoxyamine.HCl, and that the recrystallization step is not required. The title compound 13e as a brown liquid (61% yield) was obtained.
Detected Properties of the Title Compound:
IR (KBr): 3217, 1577, 1519. UV (MeOH): 372 (4.22), 260 (4.56), 208 (4.51). $^1$H NMR (400 MHz, CDCl$_3$): 2.06-2.10 (m, 4H, Pyr-H), 2.26 (s, 3H, CH$_3$), 3.24 (br s, 4H, Pyr-H), 3.35 (t, 2H, J=4.8 Hz, OCH$_2$C$\underline{H}_2$N), 4.60-4.63 (m, 2H, OC$\underline{H}_2$CH$_2$N), 6.23 (d, 1H, J=2.8 Hz, 3-H), 7.15-7.18 (m, 2H, ArH), 7.29 (br s, 1H, NH), 7.46-7.51 (m, 2H, 2-H, 6-H), 7.63-7.66 (m, 2H, ArH), 7.69-7.73 (m, 1H, 7-H), 8.07-8.14 (m, 2H, 8-H, 5-H). $^{13}$C NMR (100 MHz, CDCl$_3$): 12.87, 23.27 (2C), 53.80, 54.27 (2C), 69.56, 105.71, 106.51, 118.65, 120.44 (2C), 121.11, 123.86, 127.10 (2C), 129.10, 129.24, 130.76, 140.15, 142.48, 142.92, 146.00, 155.58, 163.22. Anal. Calc. for $C_{25}H_{26}N_4O_2$·1.0 $H_2O$·1.0HCl: C, 64.03; H, 6.23; N, 11.95. found: C, 64.19; H, 6.44; N, 11.87. HRMS (ESI): cacl. for $C_{25}H_{27}N_4O_2$ $[M+H]^+$: 415.2134. found: 415.2135.

Synthesis Ex. 6

(E)-1-(4-(Furo[2,3-b]quinolin-4-ylamino)phenyl) ethanone O-2-(piperidin-1-yl)ethyl oxime (Compound 13f)

The title compound 13f was synthesized substantially according to the procedures as set forth in the above Synthesis Example 1, except that 2-piperidin-1-ylethoxyamine.HCl was used in place of 2-aminoethoxyamine.HCl, and that the recrystallization step is not required. The title compound 13f as a brown liquid (85% yield) was obtained.
Detected Properties of the Title Compound:
IR (KBr): 3221, 1579, 1519. UV (MeOH): 368 (4.15), 260 (4.51), 206 (4.51). $^1$H NMR (400 MHz, CDCl$_3$): 1.44-1.48 (m, 2H, Pip-H), 1.57-1.65 (m, 4H, Pip-H), 2.25 (s, 3H, CH$_3$), 2.53-2.78 (m, 4H, Pip-H), 3.81 (t, 2H, J=5.6 Hz, OCH$_2$C$\underline{H}_2$N), 4.37 (t, 2H, J=6.0 Hz, OC$\underline{H}_2$CH$_2$N), 6.18 (d, 1H, J=2.4 Hz, 3-H), 7.02 (br s, 1H, NH), 7.14-7.17 (m, 2H, ArH), 7.46-7.50 (m, 2H, 2-H, 6-H), 7.66-7.73 (m, 3H, 7-H, ArH), 8.05-8.10 (m, 2H, 0.8-H, 5-H). $^{13}$C NMR (100 MHz, CDCl$_3$): 12.65, 24.13, 25.79, 25.87, 54.89, 54.93, 57.85, 72.18, 105.72, 106.06, 118.34, 120.72, 120.94 (2C), 123.78, 127.04 (2C), 129.17 (2C), 132.11, 140.38, 141.71, 142.77, 145.99, 153.83, 163.28. HRMS (ESI): cacl. for $C_{26}H_{29}N_4O_2$ $[M+H]^+$: 429.2290. found: 429.2292.

Synthesis Ex. 7

(E)-1-(4-(Furo[2,3-b]quinolin-4-ylamino)phenyl) ethanone O-2-morpholinoethyl oxime (Compound 13g)

The title compound 13g was synthesized substantially according to the procedures as set forth in the above Synthesis Example 1, except that 2-morpholinoethoxyamine.HCl was used in place of 2-aminoethoxyamine.HCl. The title compound 13g as a light yellow solid (73% yield) was obtained.
Detected Properties of the Title Compound:
M.p.: 59-62° C. IR (KBr): 3269, 1578, 1518. UV (MeOH): 372 (4.33), 260 (4.67), 208 (4.62). $^1$H NMR (400 MHz, CDCl$_3$): 2.25 (s, 3H, CH$_3$), 2.58-2.60 (m, 4H, Mor-H), 2.78 (t, 2H, J=5.6 Hz, OCH$_2$C$\underline{H}_2$N), 3.73-3.76 (m, 4H, Mor-H), 4.37 (t, 2H, J=5.6 Hz, OC$\underline{H}_2$CH$_2$N), 6.18 (d, 1H, J=2.8 Hz, 3-H), 6.97 (br s, 1H, NH), 7.14-7.17 (m, 2H, ArH), 7.46-7.50 (m, 2H, 2-H, 6-H), 7.66-7.73 (m, 3H, 7-H, ArH), 8.04-8.10 (m, 2H, 8-H, 5-H). $^{13}$C NMR (100 MHz, CDCl$_3$): 12.70, 54.05 (2C), 57.61, 60.95 (2C), 72.03, 105.70, 106.13, 118.36, 120.66, 120.88 (2C), 123.84, 127.06 (2C), 129.19 (2C), 131.97, 140.28, 141.78, 142.83, 145.98, 154.02, 163.26. Anal. calc. for $C_{25}H_{26}N_4O_3$·0.5 $H_2O$: C, 68.32; H, 6.19; N, 12.75. found: C, 68.20; H, 6.21; N, 12.78. HRMS (ESI): calc. for $C_{25}H_{27}N_4O_3$ $[M+H]^+$: 431.2083. found: 431.2080.

Synthesis Ex. 8

(E)-1-(4-(Furo[2,3-b]quinolin-4-ylamino)phenyl) ethanone O-4-morpholinobutyl oxime (Compound 13h)

The title compound 13h was synthesized substantially according to the procedures as set forth in the above Synthesis Example 1, except that 4-morpholinobutoxyamine.HCl was used in place of 2-aminoethoxyamine.HCl. The title compound 13h as a light yellow solid (73% yield) was obtained.
Detected Properties of the Title Compound:
M.p.: 87-88° C. IR (KBr): 3263, 1579, 1518. UV (MeOH): 368 (4.23), 260 (4.60), 208 (4.57). $^1$H NMR (400 MHz, CDCl$_3$): 1.62-1.79 (m, 4H, OCH$_2$C$\underline{H}_2$)$_2$CH$_2$N), 2.25 (s, 3H, CH$_3$), 2.38-2.46 (m, 6H, OCH$_2$(CH$_2$)$_2$C$\underline{H}_2$N, Mor-H), 3.72-3.74 (m, 4H, Mor-H), 4.23 (t, 2H, J=5.6 Hz, OC$\underline{H}_2$(CH$_2$)$_2$CH$_2$N), 6.16 (d, 1H, J=2.8 Hz, 3-H), 7.06 (br s, 1H, NH), 7.14-7.16 (m, 2H, ArH), 7.45-7.46 (m, 2H, 2-H, 6-H), 7.66-7.70 (m, 3H, 7-H, ArH), 8.04-8.09 (m, 2H, 8-H, 5-H). $^{13}$C NMR (100 MHz, CDCl$_3$): 12.54, 23.07, 27.18, 53.68 (2C), 58.82, 66.93 (2C), 73.94, 105.72, 105.99, 118.30, 120.69, 121.00 (2C), 123.78, 126.99 (2C), 129.14, 129.18, 132.23, 140.42, 141.64, 142.74, 145.96, 153.60, 163.27. Anal. calc. for $C_{27}H_{30}N_4O_3$·0.8 $H_2O$: C, 68.56; H, 6.73; N, 11.84. found: C, 68.47; H, 6.94; N, 11.81. HRMS (ESI): calc. for $C_{27}H_{31}N_4O_3$ $[M+H]^+$: 459.2396. found: 459.2399.

Synthesis Ex. 9

(E)-1-(4-(3-Chlorofuro[2,3-b]quinolin-4-ylamino) phenyl)ethanone O-2-aminoethyl oxime (Compound 14a)

1-(4-(3-chlorofuro[2,3-b]quinolin-4-ylamino)phenyl) ethanone (compound 10) was prepared according to the method as described in Chen Y. L. et al. (2005), *Eur. J. Med. Chem.*, 40:928-934. The thus obtained compound 10 (0.30 g, 1 mmol), 2-aminoethoxyamine.HCl (0.28 g, 2.5 mmol), and $K_2CO_3$ (0.69 g, 5.0 mmol) were added into EtOH (10 mL). The resultant mixture was subjected to reflux for 4 hours (TLC monitoring), followed by evaporation under reduced pressure. The residue thus acquired was dissolved in CH$_2$Cl$_2$ (50 mL). The CH$_2$Cl$_2$ layer was washed sequentially with H$_2$O and brine, was dried using Na$_2$SO$_4$, and was subjected to an evaporation treatment. The resultant residue was purified via flash column chromatography (MeOH/CH$_2$Cl$_2$=1/50), followed by recrystallization from EtOH. The title compound 14a as a yellow solid (95% yield) was obtained.
Detected Properties of the Title Compound:
M.p.: 169-172° C. IR (KBr): 3146, 1580, 1514. UV (MeOH): 382 (4.09), 264 (4.32), 236 (4.53), 208 (4.52). $^1$H NMR (400 MHz, CDCl$_3$): 2.22 (s, 3H, CH$_3$), 3.04 (t, 2H, J=5.2 Hz, OCH$_2$CH$_2$N), 4.22 (t. 2H, J=5.2 Hz, OCH$_2$CH$_2$N), 6.86-6.89 (m, 2H, ArH), 7.18 (br s, 1H, NH), 7.29-7.34 (m, 1H, 6-H), 7.53-7.56 (m, 2H, ArH), 7.66-7.70 (m, 2H, 2-H, 7-H), 7.81 (dd, 1H, J=8.8, 0.8 Hz, 5-H), 8.06 (d, J=8.8 Hz, 8-H). $^{13}$C NMR (100 MHz, CDCl$_3$): 12.56, 41.55, 75.66, 107.99, 110.11, 118.09 (2C), 120.05, 123.99, 124.41, 127.11 (2C), 129.09, 129.89, 130.68, 140.65, 141.53, 144.62, 146.77, 154.44, 160.73. Anal. calc. for $C_{21}H_{19}ClN_4O_2 \cdot 0.4 H_2O$: C, 62.74; H, 4.96; N, 13.94. found: C, 62.40; H, 5.17; N, 13.76. HRMS (ESI): calc. for $C_{21}H_{20}ClN_4O_2$ [M+H]$^+$: 395.1275. found: 395.1274.

Synthesis Ex. 10

(E)-1-(4-(3-Chlorofuro[2,3-b]quinolin-4-ylamino) phenyl)ethanone O-2-(dimethylamino)ethyl oxime (Compound 14b)

The title compound 14b was synthesized substantially according to the procedures as set forth in the above Synthesis Example 9, except that 2-dimethylaminoethoxyamine.HCl was used in place of 2-aminoethoxyamine.HCl. The title compound 14b as a yellow solid (97% yield) was obtained.
Detected Properties of the Title Compound:
M.p.: 118-122° C. IR (KBr): 3398, 1578, 1520. UV (MeOH): 382 (4.12), 264 (4.33), 234 (4.50), 210 (4.48). $^1$H NMR (400 MHz, CDCl$_3$): 2.22 (s, 3H, CH$_3$), 2.51 (s, 6H, N(CH$_3$)$_2$), 2.94 (t, 2H, J=5.4 Hz, OCH$_2$CH$_2$N), 4.42 (t, 2H, J=5.4 Hz, OCH$_2$CH$_2$N), 6.86-6.90 (m, 2H, ArH), 7.19 (br s, 1H, NH), 7.32-7.36 (m, 1H, 6-H), 7.53-7.56 (m, 2H, ArH), 7.67-7.71 (m, 2H, 2-H, 7-H), 7.83-7.86 (m, 1H, 5-H), 8.07-8.09 (m, 1H, 8-H). $^{13}$C NMR (100 MHz, CDCl$_3$): 12.78, 45.10 (2C), 57.48, 70.87, 110.10, 117.10, 118.01 (2C), 120.09, 124.02, 124.39, 127.14 (2C), 129.10, 129.91, 130.38, 140.70, 141.44, 144.75, 146.75, 154.77, 160.72. Anal. calc. for $C_{23}H_{23}ClN_4O_2 \cdot 1.5 H_2O$: C, 61.40; H, 5.83; N, 12.45. found: C, 61.17; H, 5.98; N, 12.09. HRMS (ESI): calc. for $C_{23}H_{24}ClN_4O_2$ [M+H]$^+$: 423.1588. found: 423.1587.

Synthesis Ex. 11

(E)-1-(4-(3-Chlorofuro[2,3-b]quinolin-4-ylamino) phenyl)ethanone O-3-aminopropyl oxime (Compound 14c)

The title compound 14c was synthesized substantially according to the procedures as set forth in the above Synthesis Example 9, except that 3-aminopropoxyamine.HCl was used in place of 2-aminoethoxyamine.HCl. The title compound 14c as a deep brown solid (98% yield) was obtained.
Detected Properties of the Title Compound:
M.p.: 114-116° C. IR (KBr): 3143, 1579, 1512. UV (MeOH): 382 (4.11), 264 (4.32), 234 (4.50), 210 (4.49). $^1$H NMR (400 MHz, CDCl$_3$): 1.92 (quin, 2H, J=6.4 Hz, OCH$_2$CH$_2$CH$_2$N), 2.19 (s, 3H, CH$_3$), 2.90 (t, 2H, J=6.8 Hz, OCH$_2$CH$_2$CH$_2$N), 4.26 (t, 2H, J=6.0 Hz, OCH$_2$CH$_2$CH$_2$N), 6.87-6.90 (m, 2H, ArH), 7.19 (br s, 1H, NH), 7.30-7.34 (m, 1H, 6-H), 7.53-7.56 (m, 2H, ArH), 7.66-7.70 (m, 2H, 2-H, 7-H), 7.82 (dd, 1H, J=8.4, 1.0 Hz, 5-H), 8.06 (d, 1H, J=8.4 Hz, 8-H). $^{13}$C NMR (100 MHz, CDCl$_3$): 12.55, 32.43, 39.09, 71.75, 107.94, 110.13, 118.16 (2C), 120.04, 123.98, 124.43, 127.09 (2C), 129.08, 129.90, 130.83, 140.63, 141.61, 144.56, 146.78, 154.02, 160.75. HRMS (ESI): calc. for $C_{22}H_{22}ClN_4O_2$ [M+H]$^+$: 409.1431. found: 409.1430.

Synthesis Ex. 12

(E)-1-(4-(3-Chlorofuro[2,3-b]quinolin-4-ylamino) phenyl)ethanone O-3-(dimethylamino)propyl oxime (Compound 14d)

The title compound 14d was synthesized substantially according to the procedures as set forth in the above Synthesis Example 9, except that 3-dimethylaminopropoxyamine.HCl was used in place of 2-aminoethoxyamine.HCl. The title compound 14d as a yellow solid (96% yield) was obtained.
Detected Properties of the Title Compound:
M.p.: 104-106° C. IR (KBr): 3147, 1578, 1520. UV (MeOH): 382 (4.17), 266 (4.45), 236 (4.62), 208 (4.59). $^1$H NMR (400 MHz, CDCl$_3$): 1.87-1.94 (m, 2H, OCH$_2$CH$_2$CH$_2$N), 2.20 (s, 3H, CH$_3$), 2.26 (s, 6H, N(CH$_3$)$_2$), 2.39-2.42 (m, 2H, OCH$_2$CH$_2$CH$_2$N), 4.21 (t, 2H, J=6.4 Hz, OCH$_2$CH$_2$CH$_2$N), 6.87-6.90 (m, 2H, ArH), 7.18 (br s, 1H, NH), 7.30-7.34 (m, 1H, 6-H), 7.54-7.57 (m, 2H, ArH), 7.66-7.70 (m, 2H, 2-H, 7-H), 7.82 (dd, 1H, J=8.6, 1.0 Hz, 5-H), 8.06 (d, 1H, J=8.4 Hz, 8-H). $^{13}$C NMR (100 MHz, CDCl$_3$): 12.49, 27.52, 45.44 (2C), 56.52, 72.29, 107.86, 110.11, 118.18 (2C), 119.99, 123.94, 124.46, 127.06 (2C), 129.08, 129.87, 131.04, 140.58, 141.65, 144.43, 146.80, 153.75, 160.74. Anal. calc. for $C_{24}H_{25}ClN_4O_2 \cdot 0.5 H_2O$: C, 64.64; H, 5.88; N, 12.56. found: C, 64.41; H, 6.03; N, 12.77. HRMS (ESI): calc. for $C_{24}H_{26}ClN_4O_2$ [M+H]$^+$: 437.1744. found: 437.1747.

Synthesis Ex. 13

(E)-1-(4-(3-Chlorofuro[2,3-b]quinolin-4-ylamino) phenyl)ethanone O-2-(pyrrolidin-1-yl)ethyl oxime (Compound 14e)

The title compound 14e was synthesized substantially according to the procedures as set forth in the above Synthesis Example 9, except that 2-pyrrolidin-1-ylethoxyamine.HCl was used in place of 2-aminoethoxyamine.HCl. The title compound 14e as a yellow solid (92% yield) was obtained.
Detected Properties of the Title Compound:
M.p.: 208-210° C. IR (KBr): 3241, 1578, 1513. UV (MeOH): 382 (4.15), 286 (4.31), 264 (4.37), 236 (4.58). $^1$H NMR (400 MHz, CDCl$_3$): 2.12 (br s, 4H, Pyr-H), 2.22 (s, 3H, CH$_3$), 3.32-3.40 (m, 6H, Pyr-H, OCH$_2$CH$_2$N), 4.62-4.65 (m, 2H, OCH$_2$CH$_2$N), 6.87-6.90 (m, 2H, ArH), 7.19 (br s, 1H, NH), 7.33-7.37 (m, 1H, 6-H), 7.53-7.56 (m, 2H, ArH), 7.68-7.73 (m, 2H, 2-H, 7-H), 7.84-7.87 (m, 1H, 5-H), 8.08-8.10 (m, 1H, 8-H). $^{13}$C NMR (100 MHz, CDCl$_3$): 12.86, 23.26 (2C), 53.66, 54.20 (2C), 69.26, 108.36, 110.10, 117.80 (2C), 120.27, 124.12, 124.28, 127.20 (2C), 129.16, 129.68, 129.94, 140.85, 141.21, 145.15, 146.75, 155.76, 160.72. Anal. calc. for $C_{25}H_{25}ClN_4O_2 \cdot 0.2 H_2O \cdot 1.0 HCl$: C, 61.40; H, 5.44; N, 11.46. found: C, 61.61; H, 5.64; N, 11.16. HRMS (ESI): calc. for $C_{25}H_{26}ClN_4O_2$ [M+H]$^+$: 449.1744. found: 449.1746.

Synthesis Ex. 14

(E)-1-(4-(3-Chlorofuro[2,3-b]quinolin-4-ylamino) phenyl)ethanone O-2-(piperidin-1-yl)ethyl oxime (Compound 14f)

The title compound 14f was synthesized substantially according to the procedures as set forth in the above Synthesis Example 9, except that 2-piperidin-1-ylethoxyamine.HCl was used in place of 2-aminoethoxyamine.HCl. The title compound 14f as a yellow solid (69% yield) was obtained.
Detected Properties of the Title Compound:
M.p.: 136-138° C. IR (KBr): 3386, 1578, 1516. UV (MeOH): 382 (4.17), 266 (4.49), 236 (4.62), 206 (4.66). $^1$H NMR (400 MHz, CDCl$_3$): 1.41-1.65 (m, 6H, Pip-H), 2.20 (s, 3H, CH$_3$), 2.52 (br s, 4H, Pip-H), 2.75 (t, 2H, J=6.0 Hz, OCH$_2$CH$_2$N), 4.23 (t, 2H, J=6.2 Hz, OCH$_2$CH$_2$N), 6.86-6.90 (m, 2H, ArH), 7.18 (br s, 1H, NH), 7.30-7.35 (m, 1H, 6-H), 7.54-7.57 (m, 2H, Ar—H), 7.67-7.57 (m, 2H, 2-H, 7-H), 7.82-7.86 (m, 1H, 5-H), 8.06-8.09 (m, 1H, 8-H). $^{13}$C NMR (100 MHz, CDCl$_3$): 12.65, 24.08, 25.80 (2C), 54.88 (2C), 57.78, 72.01, 107.91, 110.10, 118.13 (2C), 120.00, 123.95, 124.44, 127.08 (2C), 129.08, 129.87, 130.86, 140.61, 141.59, 144.49, 146.77, 153.96, 160.73. Anal. calc. for C$_{26}$H$_{27}$ClN$_4$O$_2$.1.1 H$_2$O.1.0HCl: C, 60.14; H, 5.86; N, 10.79. found: C, 59.92; H, 6.12; N, 10.47. HRMS (ESI): calc. for C$_{26}$H$_{28}$ClN$_4$O$_2$[M+H]$^+$: 463.1901. found: 463.1904.

Synthesis Ex. 15

(E)-1-(4-(3-Chlorofuro[2,3-b]quinolin-4-ylamino) phenyl)ethanone O-2-morpholinoethyl oxime (Compound 14g)

The title compound 14g was synthesized substantially according to the procedures as set forth in the above Synthesis Example 9, except that 2-morpholinoethoxyamine.HCl was used in place of 2-aminoethoxyamine.HCl. The title compound 14g as a light yellow solid (96% yield) was obtained.
Detected Properties of the Title Compound:
M.p.: 118-121° C. IR (KBr): 3391, 1579, 1514. UV (MeOH): 382 (4.11), 264 (4.34), 234 (4.50), 210 (4.49). $^1$H NMR (400 MHz, CDCl$_3$): 2.19 (s, 3H, CH$_3$), 2.54-2.57 (m, 4H, Mor-H), 2.75 (t, 2H, J=5.6 Hz, OCH$_2$CH$_2$N), 3.72-3.74 (m, 4H, Mor-H), 4.33 (t, 2H, J=5.6 Hz, OCH$_2$CH$_2$N), 6.86-6.89 (m, 2H, ArH), 7.18 (br s, 1H, NH), 7.28-7.33 (m, 1H, 6-H), 7.52-7.56 (m, 2H, ArH), 7.67-7.70 (m, 2H, 2-H, 7-H), 7.81 (dd, 1H, J=8.8, 0.8 Hz, 5-H), 8.06 (dd, 1H, J=8.6, 0.6 Hz, 8-H). $^{13}$C NMR (100 MHz, CDCl$_3$): 12.63, 53.98 (2C), 57.54, 66.90 (2C), 71.87, 107.97, 110.06, 117.97 (2C), 120.03, 123.91, 124.33, 127.03 (2C), 129.00, 129.82, 130.60, 140.60, 141.44, 144.56, 146.67, 154.03, 160.66. Anal. calc. for C$_{25}$H$_{25}$ClN$_4$O$_3$.1.0 H$_2$O.0.5HCl: C, 59.91; H, 5.53; N, 11.18. found: C, 60.05; H, 5.68; N, 10.88. HRMS (ESI): calc. for C$_{25}$H$_{26}$ClN$_4$O$_3$ [M+H]$^+$: 465.1693. found: 465.1695.

Synthesis Ex. 16

(E)-1-(4-(3-Chlorofuro[2,3-b]quinolin-4-ylamino) phenyl)ethanone O-4-morpholinobutyl oxime (Compound 14h)

The title compound 14h was synthesized substantially according to the procedures as set forth in the above Synthesis Example 9, except that 4-morpholinobutoxyamine.HCl was used in place of 2-aminoethoxyamine.HCl. The title compound 14h as a yellow solid (86% yield) was obtained.
Detected Properties of the Title Compound:
M.p.: 112-113° C. IR (KBr): 3138, 1614, 1580, 1512. UV (MeOH): 382 (4.14), 266 (4.45), 236 (4.58), 206 (4.56). $^1$H NMR (400 MHz, CDCl$_3$): 1.60-1.77 (m, 4H, OCH$_2$(CH$_2$)$_2$CH$_2$N), 2.20 (s, 3H, CH$_3$), 2.40 (t, 2H, J=7.6 Hz, OCH$_2$(CH$_2$)$_2$CH$_2$N), 2.46 (br s, 4H, Mor-H), 3.72-3.74 (m, 4H, Mor-H), 4.19 (t, 2H, J=6.4 Hz, OCH$_2$(CH$_2$)$_2$CH$_2$N), 6.86-6.90 (m, 2H, ArH), 7.17 (br s, 1H, NH), 7.30-7.34 (m, 1H, 6-H), 7.53-7.57 (m, 2H, ArH), 7.66-7.71 (m, 2H, 2-H), 7.82 (dd, 1H, J=8.4, 1.2 Hz, 5-H), 8.06 (dd, 1H, J=8.4, 0.4 Hz, 5-H). $^{13}$C NMR (100 MHz, CDCl$_3$): 12.53, 23.04, 27.17 (2C), 53.67 (2C), 58.82, 66.90, 73.84, 107.90, 110.12, 118.19 (2C), 120.01, 123.95, 124.45, 127.06 (2C), 129.11, 129.87, 131.04, 140.61, 141.63, 144.46, 146.81, 153.70, 160.75. Anal. calc. for C$_{27}$H$_{29}$ClN$_4$O$_3$.0.3 H$_2$O: C, 65.06; H, 5.99; N, 11.24. found: C, 64.96; H, 6.25; N, 11.07. HRMS (ESI): calc. for C$_{27}$H$_{30}$ClN$_4$O$_3$ [M+H]$^+$: 493.2006. found: 493.2004.

Synthesis Ex. 17

(E)-1-(4-(7-Methoxyfuro[2,3-b]quinolin-4-ylamino) phenyl)ethanone O-2-aminoethyl oxime (Compound 15a)

1-(4-(7-methoxyfuro[2,3-b]quinolin-4-ylamino)phenyl) ethanone (compound 11), was prepared according to the method as described in Chen Y. L. et al. (2005), *Eur. J. Med. Chem.*, 40:928-934. The thus obtained compound 11 (0.33 g, 1 mmol), 2-aminoethoxyamine.HCl (0.28 g, 2.5 mmol), and K$_2$CO$_3$ (0.69 g, 5.0 mmol) were added into EtOH (10 mL). The resultant mixture was subjected to reflux for 4 hours (TLC monitoring), followed by evaporation under reduced pressure. The residue thus acquired was dissolved in CH$_2$Cl$_2$ (50 mL). The CH$_2$Cl$_2$ layer was washed sequentially with H$_2$O and brine, was dried using Na$_2$SO$_4$, and was subjected to an evaporation treatment. The resultant residue was purified via flash column chromatography (MeOH/CH$_2$Cl$_2$=1/50), followed by recrystallization from EtOH. The title compound 15a as a deep green solid (0.26 g, 66% yield) was obtained.
Detected Properties of the Title Compound:
M.p.: 91-93° C. IR (KBr): 3219, 1581, 1517. UV (MeOH): 358 (4.22), 248 (4.44), 212 (4.48). $^1$H NMR (400 MHz, DMSO-d$_6$): 2.22 (s, 3H, CH$_3$), 2.88 (t, 2H, J=5.8 Hz, OCH$_2$CH$_2$N), 3.92 (s, 3H, OCH$_3$), 4.12 (t, 2H, J=5.8 Hz, OCH$_2$CH$_2$N), 6.08 (d, 1H, J=2.4 Hz, 3-H), 7.13-7.19 (m, 3H, 6-H, ArH), 7.29 (d, 1H, J=2.4 Hz, 2-H), 7.66-7.69 (m, 2H, ArH), 7.74 (d, 1H, J=2.8 Hz, 8-H), 8.27 (d, 1H, J=9.6 Hz, 5-H), 9.48 (br s, 1H, NH). $^{13}$C NMR (100 MHz, DMSO-d$_6$): 12.20, 40.72, 55.35, 75.17, 103.70, 105.72, 106.75, 113.14, 115.49, 120.69 (2C), 124.39, 126.59 (2C), 130.28, 141.47, 142.06, 142.73, 147.70, 153.70, 160.09, 163.44. HRMS (ESI): calc. for C$_{22}$H$_{23}$N$_4$O$_3$ [M+H]$^+$: 391.1770. found: 391.1769.

Synthesis Ex. 18

(E)-1-(4-(7-Methoxyfuro[2,3-b]quinolin-4-ylamino) phenyl)ethanone O-2-(dimethylamino)ethyl oxime (Compound 15b)

The title compound 15b was synthesized substantially according to the procedures as set forth in the above Synthesis Example 17, except that 2-dimethylaminoethoxyamine.HCl was used in place of 2-aminoethoxyamine.HCl. The title compound 15b as a light yellow solid (88% yield) was obtained.
Detected Properties of the Title Compound:
M.p.: 150-152° C. IR (KBr): 3256, 1580, 1518. UV (MeOH): 360 (4.26), 250 (4.47), 210 (4.50). $^1$H NMR (400 MHz, CDCl$_3$): 2.26 (s, 3H, CH$_3$), 2.36 (s, 6H, N(CH$_3$)$_2$), 2.75 (t, 2H, J=5.8 Hz, OCH$_2$CH$_2$N), 3.95 (s, 3H, OCH$_3$), 4.34 (t, 2H, J=5.8 Hz, OCH$_2$CH$_2$N), 6.16 (d, 1H, J=2.4 Hz, 3-H), 6.95 (br s, 1H, NH), 7.10-7.15 (m, 3H, 6-H, ArH), 7.39 (d, 1H, J=2.4 Hz, 2-H), 7.40 (d, 1H, J=2.8 Hz, 8-H), 7.65-7.68 (m, 2H, ArH), 7.92 (d, 1H, J=9.2 Hz, 5-H). $^{13}$C NMR (100 MHz, CDCl$_3$): 12.70, 45.85 (2C), 55.48, 58.17, 72.21, 104.80, 105.74, 107.20, 113.24, 116.74, 120.72 (2C), 122.04, 127.04 (2C), 131.86, 140.47, 141.80, 141.87, 148.04, 154.04, 160.57, 163.85. Anal. calc. for C$_{24}$H$_{26}$N$_4$O$_3$.0.5 H$_2$O: C, 67.43; H, 6.37; N, 13.11. found: C, 67.43; H, 6.58; N, 12.83. HRMS (ESI): calc. for C$_{24}$H$_{27}$N$_4$O$_3$ [M+H]$^+$: 419.2083. found: 419.2086.

Synthesis Ex. 19

(E)-1-(4-(7-Methoxyfuro[2,3-b]quinolin-4-ylamino) phenyl)ethanone O-3-aminopropyl oxime (Compound 15c)

The title compound 15c was synthesized substantially according to the procedures as set forth in the above Synthesis Example 17, except that 3-aminopropoxyamine.HCl was used in place of 2-aminoethoxyamine.HCl, and that the recrystallization step is not required. The title compound 15c as a light yellow liquid (68% yield) was obtained.
Detected Properties of the Title Compound:
IR (KBr): 3220, 1582, 1518. UV (MeOH): 362 (4.12), 260 (4.35), 210 (4.40). $^1$H NMR (400 MHz, DMSO-d$_6$): 1.82 (quin, 2H, J=6.6 Hz, OCH$_2$CH$_2$CH$_2$N), 2.20 (s, 3H, CH$_3$), 2.73 (t, 2H, J=6.8 Hz, OCH$_2$CH$_2$CH$_2$N), 3.92 (s, 1H, OCH$_3$), 4.19 (t, 2H, J=6.4 Hz, OCH$_2$CH$_2$CH$_2$N), 6.08 (d, 1H, J=2.4 Hz, 3-H), 7.12-7.18 (m, 3H, 6-H, ArH), 7.28 (d, 1H, J=2.4 Hz, 2-H), 7.66-7.69 (m, 2H, ArH), 7.74 (d, 1H, J=2.8 Hz, 8-H), 8.28 (d, 1H, J=9.6 Hz, 5-H), 9.50 (br s, 1H, NH). $^{13}$C NMR (100 MHz, DMSO-d$_6$): 12.11, 31.28, 37.87, 55.34, 71.14, 103.68, 105.72, 106.74, 113.14, 115.46, 120.68 (2C), 124.40, 126.54 (2C), 130.29, 141.47, 142.05, 142.71, 147.70, 153.36, 160.08, 163.43. HRMS (ESI): calc. for C$_{23}$H$_{25}$N$_4$O$_3$ [M+H]$^+$: 405.1927. found: 405.1926.

Synthesis Ex. 20

(E)-1-(4-(7-Methoxyfuro[2,3-b]quinolin-4-ylamino) phenyl)ethanone O-3-(dimethylamino)propyl oxime (Compound 15d)

The title compound 15d was synthesized substantially according to the procedures as set forth in the above Synthesis Example 17, except that 3-dimethylaminopropoxyamine.HCl was used in place of 2-aminoethoxyamine.HCl. The title compound 15d as a light yellow solid (79% yield) was obtained.
Detected Properties of the Title Compound:
M.p.: 95-97° C. IR (KBr): 3327, 1580, 1516. UV (MeOH): 364 (4.32), 264 (4.60), 206 (4.61). $^1$H NMR (400 MHz, DMSO-d$_6$): 1.82 (quin, 2H, J=6.6 Hz, OCH$_2$CH$_2$CH$_2$N), 2.18 (s, 6H, N(CH$_3$)$_2$), 2.19 (s, 3H, CH$_3$), 2.37 (t, 2H, J=7.2 Hz, OCH$_2$CH$_2$CH$_2$N), 3.92 (s, 1H, OCH$_3$), 4.15 (t, 2H, J=6.4 Hz, OCH$_2$CH$_2$CH$_2$N), 6.08 (d, 1H, J=2.8 Hz, 3-H), 7.13-7.19 (m, 3H, 6-H, ArH), 7.29 (d, 1H, J=2.4 Hz, 2-H), 7.66-7.68 (m, 2H, ArH), 7.74 (d, 1H, J=2.8 Hz, 8-H), 8.27 (d, 1H, J=9.2 Hz, 5-H), 9.47 (br s, 1H, NH). $^{13}$C NMR (100 MHz, DMSO-d$_6$): 12.11, 26.81, 44.97 (2C), 55.34, 55.67, 71.60, 103.68, 105.72, 106.75, 113.13, 115.46, 120.69 (2C), 124.38, 126.54 (2C), 130.33, 141.47, 142.05, 142.68, 147.70, 153.31, 160.08, 163.43. Anal. calc. for C$_{26}$H$_{28}$N$_4$O$_3$.1.2 H$_2$O: C, 66.12; H, 6.75; N, 12.34. found: C, 66.28; H, 6.82; N, 12.08. HRMS (ESI): calc. for C$_{26}$H$_{29}$N$_4$O$_3$ [M+H]$^+$: 433.2240. found: 433.2243.

Synthesis Ex. 21

(E)-1-(4-(7-Methoxyfuro[2,3-b]quinolin-4-ylamino) phenyl)ethanone O-2-(pyrrolidin-1-yl)ethyl oxime (Compound 15e)

The title compound 15e was synthesized substantially according to the procedures as set forth in the above Synthesis Example 17, except that 2-pyrrolidin-1-ylethoxyamine.HCl was used in place of 2-aminoethoxyamine.HCl. The title compound 15e as a light yellow solid (81% yield) was obtained.
Detected Properties of the Title Compound:
M.p.: 123-124° C. IR (KBr): 3244, 1585, 1525. UV (MeOH): 362 (4.28), 260 (4.50), 210 (4.54). $^1$H NMR (400 MHz, DMSO-d$_6$): 1.69-1.72 (m, 4H, Pyr-H), 2.20 (s, 3H, CH$_3$), 2.60 (br s, 4H, Pyr-H), 2.83 (t, 2H, J=5.6 Hz, OCH$_2$CH$_2$N), 3.91 (s, 3H, OCH$_3$), 4.24 (t, 2H, J=6.0 Hz, OCH$_2$CH$_2$N), 6.08 (d, 1H, J=2.8 Hz, 3-H), 7.13-7.18 (m, 3H, 6-H, ArH), 7.28 (d, 1H, J=2.8 Hz, 2-H), 7.66-7.68 (m, 2H, ArH), 7.74 (d, 1H, J=2.4 Hz, 5-H), 8.25 (d, 1H, J=9.2 Hz, 8-H), 9.47 (br s, 1H, NH). $^{13}$C NMR (100 MHz, DMSO-d$_6$): 12.33, 23.11 (2C), 54.13 (2C), 54.28, 55.40, 72.39, 103.73, 105.77, 106.75, 113.147, 115.56, 120.69 (2C), 124.42, 126.65 (2C), 130.21, 141.47, 142.13, 142.78, 147.73, 153.64, 160.12, 163.46. Anal. calc. for C$_{26}$H$_{28}$N$_4$O$_3$.1.2 H$_2$O: C, 66.99; H, 6.57; N, 12.02. found: C, 67.12; H, 6.73; N, 11.73. HRMS (ESI): calc. for C$_{26}$H$_{29}$N$_4$O$_3$ [M+H]$^+$: 445.2240. found: 445.2241.

Synthesis Ex. 22

(E)-1-(4-(7-Methoxyfuro[2,3-b]quinolin-4-ylamino) phenyl)ethanone O-2-(piperidin-1-yl)ethyl oxime (Compound 15f)

The title compound 15f was synthesized substantially according to the procedures as set forth in the above Synthesis Example 17, except that 2-piperidin-1-ylethoxyamine.HCl was used in place of 2-aminoethoxyamine.HCl. The title compound 15f as a light yellow solid (72% yield) was obtained.
Detected Properties of the Title Compound:
M.p.: 116-119° C. IR (KBr): 3221, 1618, 1585, 1526. UV (MeOH): 362 (4.35), 260 (4.57), 210 (4.59). $^1$H NMR (400 MHz, DMSO-d$_6$): 1.35-1.50 (m, 6H, Pip-H), 2.18 (s, 3H, CH$_3$), 2.42 (m, 4H, Pip-H), 2.62 (t, 2H, J=5.8 Hz, OCH$_2$CH$_2$N), 3.92 (s, 3H, OCH$_3$), 4.22 (t, 2H, J=6.0 Hz, OCH$_2$CH$_2$N), 6.07 (d, 1H, J=2.8 Hz, 3-H), 7.12-7.17 (m, 3H, 6-H, ArH), 7.29 (d, 1H, J=2.8 Hz, 2-H), 7.65-7.68 (m, 2H, ArH), 7.74 (d, 1H, J=2.8 Hz, 5-H), 8.25 (d, 1H, J=9.2 Hz, 8-H), 9.46 (br s, 1H, NH). $^{13}$C NMR (100 MHz, DMSO-d$_6$): 12.26, 23.86, 25.54 (2C), 54.40 (2C), 55.36, 57.34, 71.57, 103.70, 105.73, 106.75, 113.14, 115.49, 120.68 (2C), 124.37, 126.59 (2C), 130.24, 141.45, 142.07, 142.72, 147.70, 153.48, 160.09, 163.44. HRMS (ESI): calc. for C$_{27}$H$_{31}$N$_4$O$_3$ [M+H]$^+$: 459.2396. found: 459.2395.

Synthesis Ex. 23

(E)-1-(4-(7-Methoxyfuro[2,3-b]quinolin-4-ylamino) phenyl)ethanone O-2-morpholinoethyl oxime (Compound 15g)

The title compound 15g was synthesized substantially according to the procedures as set forth in the above Synthesis Example 17, except that 2-morpholinoethoxyamine.HCl was used in place of 2-aminoethoxyamine.HCl. The title compound 15g as a white-colored solid (80% yield) was obtained.
Detected Properties of the Title Compound:

M.p.: 148-149° C. IR (KBr): 3208, 1617, 1578, 1524. UV (MeOH): 362 (4.32), 262 (4.56), 246 (4.53), 206 (4.61). $^1$H NMR (400 MHz, DMSO-d$_6$): 2.18 (s, 3H, CH$_3$), 2.43-2.46 (m, 4H, Mor-H), 2.64 (t, 2H, J=6.0 Hz, OCH$_2$CH$_2$N), 3.57 (m, 4H, Mor-H), 3.91 (s, 3H, OCH$_3$), 4.24 (t, 2H, J=6.0 Hz, OCH$_2$CH$_2$N), 6.07 (d, 1H, J=2.8 Hz, 3-H), 7.13-7.18 (m, 3H, 6-H, ArH), 7.28 (d, 1H, J=2.4 Hz, 2-H), 7.65-7.68 (m, 2H, ArH), 7.74 (d, 1H, J=2.8 Hz, 5-H), 8.25 (d, 1H, J=9.6 Hz, 8-H), 9.46 (br s, 1H, NH). $^{13}$C NMR (100 MHz, DMSO-d$_6$): 12.33, 53.72 (2C), 55.40, 57.10, 66.24 (2C), 71.43, 103.72, 105.77, 106.75, 113.16, 115.56, 120.70 (2C), 124.41, 126.63 (2C), 130.24, 141.47, 142.12, 142.75, 147.73, 153.60, 160.12, 163.46. Anal. calc. for C$_{26}$H$_{28}$N$_4$O$_4$: C, 67.81; H, 6.13; N, 12.16. found: C, 67.98; H, 6.27; N, 11.71. HRMS (ESI): calc. for C$_{26}$H$_{29}$N$_4$O$_4$ [M+H]$^+$: 461.2189. found: 461.2187.

Synthesis Ex. 24

(E)-1-(4-(7-Methoxyfuro[2,3-b]quinolin-4-ylamino) phenyl)ethanone O-4-morpholinobutyl oxime (Compound 15h)

The title compound 15h was synthesized substantially according to the procedures as set forth in the above Synthesis Example 17, except that 4-morpholinobutoxyamine.HCl was used in place of 2-aminoethoxyamine.HCl. The title compound 15h as a white-colored solid (71% yield) was obtained.
Detected Properties of the Title Compound:

M.p.: 100-102° C. IR (KBr): 3211, 1578, 1519. UV (MeOH): 362 (4.35), 260 (4.56), 210 (4.57). $^1$H NMR (400 MHz, CDCl$_3$): 1.60-1.86 (m, 2H, OCH$_2$(CH$_2$)$_2$CH$_2$N), 2.25 (s, 3H, CH$_3$), 2.39-2.46 (m, 6H, Mor-H, OCH$_2$(CH$_2$)$_2$CH$_2$N), 3.72-3.74 (m, 4H, Mor-H), 3.95 (s, 3H, OCH$_3$), 4.22 (t, 2H, J=6.4 Hz, OCH$_2$(CH$_2$)$_2$CH$_2$N), 6.15 (d, 1H, J=2.8 Hz, 3-H), 6.90 (br s, 1H, NH), 7.10 (d, 1H, J=2.4 Hz, 6-H), 7.12-7.15 (m, 2H, ArH), 7.39 (d, 1H, J=2.8 Hz, 2-H), 7.40 (d, 1H, J=2.4 Hz, 5-H), 7.65-7.68 (m, 2H, ArH), 7.91 (d, 1H, J=9.6 Hz, 8-H). $^{13}$C NMR (100 MHz, CDCl$_3$): 12.55, 23.06, 27.18, 53.68 (2C), 55.48, 58.82, 66.91 (2C), 73.92, 104.70, 105.74, 107.18, 113.17, 116.73, 120.79 (2C), 121.98, 126.98 (2C), 132.05, 140.48, 141.74, 141.77, 148.02, 153.63, 160.56, 163.85. Anal. calc. for C$_{28}$H$_{32}$N$_4$O$_4$: C, 68.83; H, 6.60, N, 11.47. found: C, 68.94; H, 6.81; N, 11.04. HRMS (ESI): calc. for C$_{28}$H$_{33}$N$_4$O$_4$ [M+H]$^+$: 489.2502. found: 489.2503.

Synthesis Ex. 25

(E)-1-(4-(3-Chloro-7-methoxyfuro[2,3-b]quinolin-4-ylamino)phenyl)ethanone O-2-aminoethyl oxime (Compound 16a)

1-(4-(3-chloro-7-methoxyfuro[2,3-b]quinolin-4-ylamino) phenyl)ethanone (compound 12), was prepared according to the method as described in Chen Y. L. et al. (2005), *Eur. J. Med. Chem.*, 40:928-934. The thus obtained compound 12 (0.37 g, 1 mmol), 2-aminoethoxyamine.HCl (0.28 g, 2.5 mmol), and K$_2$CO$_3$ (0.69 g, 5.0 mmol) were added into EtOH (10 mL). The resultant mixture was subjected to reflux for 4 hours (TLC monitoring), followed by evaporation under reduced pressure. The residue thus acquired was dissolved in CH$_2$Cl$_2$ (50 mL). The CH$_2$Cl$_2$ layer was washed sequentially with H$_2$O and brine, was dried using Na$_2$SO$_4$, and was subjected to an evaporation treatment. The resultant residue was purified via flash column chromatography (MeOH/CH$_2$Cl$_2$=1/50), followed by recrystallization from EtOH. The title compound 16a as a yellow solid (98% yield) was obtained.
Detected Properties of the Title Compound:

M.p.: 108-110° C. IR (KBr): 3133, 1580, 1520. UV (MeOH): 374 (4.15), 246 (4.49), 210 (4.47). $^1$H NMR (400 MHz, DMSO-d$_6$): 2.14 (s, 3H, CH$_3$), 2.81 (t, 2H, J=6.4 Hz, OCH$_2$CH$_2$N), 3.94 (s, 3H, OCH$_3$), 4.05 (t, 2H, J=5.8 Hz, OCH$_2$CH$_2$N), 6.85-6.87 (m, 2H, ArH), 7.20 (dd, 1H, J=9.2, 2.4 Hz, 6-H), 7.37 (d, 1H, J=2.4 Hz, 8-H), 7.49-7.52 (m, 2H, ArH), 8.11 (d, 1H, J=9.2 Hz, 5-H), 8.24 (s, 1H, 2-H), 9.12 (br s, 1H, NH). $^{13}$C NMR (100 MHz, DMSO-d$_6$): 12.12, 41.00, 55.57, 75.65, 106.72, 107.53, 109.95, 115.74 (2C), 116.64, 117.26, 124.84, 126.80 (2C), 127.76, 140.67, 141.13, 147.02, 148.04, 153.59, 160.81, 161.35. HRMS (ESI): calc. for C$_{22}$H$_{22}$ClN$_4$O$_3$ [M+H]$^+$: 425.1380. found: 425.1382.

Synthesis Ex. 26

(E)-1-(4-(3-Chloro-7-methoxyfuro[2,3-b]quinolin-4-ylamino)phenyl)ethanone O-2-(dimethylamino) ethyl oxime (Compound 16b)

The title compound 16b was synthesized substantially according to the procedures as set forth in the above Synthesis Example 25, except that 2-dimethylaminoethoxyamine.HCl was used in place of 2-aminoethoxyamine.HCl. The title compound 16b as a deep yellow solid (88% yield) was obtained.
Detected Properties of the Title Compound:

M.p.: 102-104° C. IR (KBr): 3130, 1581, 1518. UV (MeOH): 374 (4.19), 248 (4.55), 210 (4.55). $^1$H NMR (400 MHz, CDCl$_3$): 2.21 (s, 3H, CH$_3$), 2.33 (s, 6H, N(CH$_3$)$_2$), 2.70 (t, 2H, J=6.0 Hz, OCH$_2$CH$_2$N), 3.95 (s, 3H, OCH$_3$), 4.30 (t, 2H, J=6.0 Hz, OCH$_2$CH$_2$N), 6.87-6.89 (m, 2H, ArH), 6.96 (dd, 1H, J=9.4, 2.6 Hz, 6-H), 7.12 (br s, 1H, NH), 7.36 (d, 1H, J=2.6 Hz, 8-H), 7.54-7.56 (m, 2H, ArH), 7.61 (s, 1H, 2-H), 7.68 (d, 1H, J=9.4 Hz, 5-H). $^{13}$C NMR (100 MHz, CDCl$_3$) 12.71, 45.94 (2C), 55.51, 58.22, 72.26, 106.14, 106.86, 110.11 (2C), 114.80, 117.19, 118.11, 125.66, 127.11 (2C), 130.83, 139.40, 141.64, 144.48, 149.04, 154.05, 161.00, 161.38. Anal. calc. for C$_{24}$H$_{26}$ClN$_4$O$_3$.0.2 H$_2$O: C, 63.12; H, 5.62; N, 12.27. found: C, 62.94; H, 5.64; N, 12.07. HRMS (ESI): calc. for C$_{24}$H$_{26}$ClN$_4$O$_3$ [M+H]$^+$: 453.1693. found: 453.1691.

Synthesis Ex. 27

(E)-1-(4-(3-Chloro-7-methoxyfuro[2,3-b]quinolin-4-ylamino)phenyl)ethanone O-3-aminopropyl oxime (Compound 16c)

The title compound 16c was synthesized substantially according to the procedures as set forth in the above Synthesis Example 25, except that 3-aminopropoxyamine.HCl was used in place of 2-aminoethoxyamine.HCl. The title compound 16c as a yellow solid (43% yield) was obtained.
Detected Properties of the Title Compound:

M.p.: 115-116° C. IR (KBr): 3386, 1584, 1513. UV (MeOH): 374 (4.02), 344 (4.02), 246 (4.42), 206 (4.46). $^1$H NMR (400 MHz, CDCl$_3$): 1.90 (quin, 2H, J=6.8 Hz, OCH$_2$CH$_2$CH$_2$N), 2.14 (s, 3H, CH$_3$), 2.83 (t, 2H, J=7.2 Hz, OCH$_2$CH$_2$CH$_2$N), 3.94 (s, 3H, OCH$_3$), 4.16 (t, 2H, J=6.4 Hz, OCH$_2$CH$_2$CH$_2$N), 6.84-6.77 (m, 2H, ArH), 7.21 (dd, 1H, J=9.6, 2.4 Hz, 6-H), 7.37 (d, 1H, J=2.4 Hz, 8-H), 7.47-7.52 (m, 2H, ArH), 8.14 (d, 1H, J=9.6 Hz, 5-H), 8.24 (s, 1H, 2-H), 9.18 (br s, 1H, NH). $^{13}$C NMR (100 MHz, CDCl$_3$): 12.10, 28.68, 36.91, 55.56, 70.39, 106.71, 107.56, 109.92, 115.69 (2C), 116.68, 117.55, 124.85, 126.43, 126.83 (2C), 140.63, 141.14, 147.13, 148.03, 153.81, 160.82, 161.34. HRMS (ESI): calc. for C$_{23}$H$_{24}$ClN$_4$O$_3$ [M+H]$^+$: 439.1537. found: 439.1535.

Synthesis Ex. 28

(E)-1-(4-(3-Chloro-7-methoxyfuro[2,3-b]quinolin-4-ylamino)phenyl)ethanone O-3-(dimethylamino) propyl oxime (Compound 16d)

The title compound 16d was synthesized substantially according to the procedures as set forth in the above Synthesis Example 25, except that 3-dimethylaminopropoxyamine.HCl was used in place of 2-aminoethoxyamine.HCl. The title compound 16d as a deep yellow solid (79% yield) was obtained.
Detected Properties of the Title Compound:
M.p.: 96-98° C. IR (KBr): 3247, 1615, 1583, 1523. UV (MeOH): 374 (4.20), 346 (4.17), 248 (4.55), 210 (4.56). $^1$H NMR (400 MHz, CDCl$_3$): 1.85-1.96 (m, 2H, OCH$_2$CH$_2$CH$_2$N), 2.20 (s, 3H, CH$_3$), 2.28 (s, 6H, N(CH$_3$)$_2$), 2.44 (t, 2H, J=7.6 Hz, OCH$_2$CH$_2$CH$_2$N), 3.95 (d, 3H, OCH$_3$), 4.22 (t, 2H, J=6.4 Hz, OCH$_2$CH$_2$CH$_2$N), 6.86-6.90 (m, 2H, ArH), 6.96 (dd, 1H, J=9.6, 2.6 Hz, 6-H), 7.12 (br s, 1H, NH), 7.36 (d, 1H, J=2.6 Hz, 8-H), 7.54-7.56 (m, 2H, ArH), 7.61 (s, 1H, 2-H), 7.69 (d, 1H, J=9.6 Hz, 5-H). $^{13}$C NMR (100 MHz, CDCl$_3$): 12.48, 27.40, 45.33 (2C), 55.50, 56.49, 72.20, 106.11, 106.89, 110.13, 114.80, 117.18, 118.15 (2C), 125.66, 127.08 (2C), 130.95, 139.38, 141.68, 144.43, 149.06, 153.80, 161.01, 161.39. Anal. calc. for C$_{25}$H$_{27}$ClN$_4$O$_3$.1.0 H$_2$O: C, 61.91; H, 6.03; N, 11.55. found: C, 61.61; H, 6.34; N, 11.57. HRMS (ESI): calc. for C$_{25}$H$_{28}$ClN$_4$O$_3$ [M+H]$^+$: 467.1850. found: 467.1851.

Synthesis Ex. 29

(E)-1-(4-(3-Chloro-7-methoxyfuro[2,3-b]quinolin-4-ylamino)phenyl)ethanone O-2-(pyrrolidin-1-yl)ethyl oxime (Compound 16e)

The title compound 16e was synthesized substantially according to the procedures as set forth in the above Synthesis Example 25, except that 2-pyrrolidin-1-ylethoxyamine.HCl was used in place of 2-aminoethoxyamine.HCl. The title compound 16e as a yellow solid (98% yield) was obtained.
Detected Properties of the Title Compound:
M.p.: 116-117° C. IR (KBr): 3137, 1617, 1580, 1520. UV (MeOH): 374 (4.14), 344 (4.13), 246 (4.52), 206 (4.58). $^1$H NMR (400 MHz, CDCl$_3$): 1.67-1.70 (m, 4H, Pyr-H), 2.13 (s, 3H, CH$_3$), 2.50-2.55 (m, 4H, Pyr-H), 2.76-2.79 (m, 2H, OCH$_2$CH$_2$N), 4.19 (t, 2H, J=6.0 Hz, OCH$_2$CH$_2$N), 6.84-6.88 (m, 2H, ArH), 7.20 (dd, 1H, J=9.4, 2.6 Hz, 6-H), 7.37 (d, 1H, J=2.6 Hz, 8-H), 7.48-7.52 (m, 2H, ArH), 8.12 (d, 1H, J=9.6 Hz, 5-H), 8.24 (s, 1H, 2-H), 9.13 (br s, 1H, NH). $^{13}$C NMR (100 MHz, CDCl$_3$): 12.22, 23.09 (2C), 54.07 (2C), 54.31, 55.57, 72.33, 106.72, 107.57, 109.94, 115.70 (2C), 116.66, 117.28, 124.84, 126.84 (2C), 127.62, 140.65, 141.16, 147.08, 148.04, 153.59, 160.82, 161.34. Anal. calc. for C$_{26}$H$_{27}$ClN$_4$O$_3$.0.1HCl: C, 64.70; H, 5.66; N, 11.61. found: C, 64.75; H, 6.28; N, 11.29. HRMS (ESI): calc. for C$_{26}$H$_{28}$ClN$_4$O$_3$ [M+H]$^+$: 479.1850. found: 479.1852.

Synthesis Ex. 30

(E)-1-(4-(3-Chloro-7-methoxyfuro[2,3-b]quinolin-4-ylamino)phenyl)ethanone O-2-(piperidin-1-yl)ethyl oxime (Compound 16f)

The title compound 16f was synthesized substantially according to the procedures as set forth in the above Synthesis Example 25, except that 2-piperidin-1-ylethoxyamine.HCl was used in place of 2-aminoethoxyamine.HCl. The title compound 16f as a yellow solid (98% yield) was obtained.
Detected Properties of the Title Compound:
M.p.: 126-127° C. IR (KBr): 3135, 1617, 1580, 1521. UV (MeOH): 374 (4.13), 346 (4.12), 246 (4.47), 210 (4.47). $^1$H NMR (400 MHz, CDCl$_3$): 1.34-1.38 (m, 2H, Pip-H), 1.44-1.51 (m, 4H, Pip-H), 2.11 (s, 3H, CH$_3$), 2.37-2.46 (br s, 4H, Pip-H), 3.60 (t, 2H, J=5.6 Hz, OCH$_2$CH$_2$N), 3.93 (s, 3H, OCH$_3$), 4.17 (t, 2H, J=2.6 Hz, OCH$_2$CH$_2$N), 6.83-6.87 (m, 2H, ArH), 7.20 (dd, 1H, J=9.4, 2.6 Hz, 6-H), 7.36 (d, 1H, J=2.6 Hz, 8-H), 7.48-7.51 (m, 2H, ArH), 8.11 (d, 1H, J=9.4 Hz, 5-H), 8.24 (s, 1H, 2-H), 9.12 (br s, 1H, NH). $^{13}$C NMR (100 MHz, CDCl$_3$): 12.24, 23.86, 25.52 (2C), 54.40 (2C), 55.60, 57.39, 71.39, 106.73, 107.58, 109.96, 115.72 (2C), 116.67, 117.31, 124.86, 126.86 (2C), 127.67, 140.67, 141.18, 147.08, 148.06, 153.59, 160.84, 161.36. Anal. calc. for C$_{27}$H$_{29}$ClN$_4$O$_3$.0.4 H$_2$O: C, 64.83; H, 6.00; N, 11.20. found: C, 64.78; H, 6.31, N 11.08. HRMS (ESI): calc. for C$_{27}$H$_{30}$ClN$_4$O$_3$ [M+H]$^+$: 493.2006. found: 493.2005.

Synthesis Ex. 31

(E)-1-(4-(3-Chloro-7-methoxyfuro[2,3-b]quinolin-4-ylamino)phenyl)ethanone O-2-morpholinoethyl oxime (Compound 16g)

The title compound 16g was synthesized substantially according to the procedures as set forth in the above Synthesis Example 25, except that 2-morpholinoethoxyamine.HCl was used in place of 2-aminoethoxyamine.HCl. The title compound 16g as a light yellow solid (99% yield) was obtained.
Detected Properties of the Title Compound:
M.p.: 99-101° C. IR (KBr): 3149, 1613, 1582, 1522. UV (MeOH): 374 (4.12), 344 (4.11), 248 (4.55), 206 (4.63). $^1$H NMR (400 MHz, CDCl$_3$): 2.13 (s, 3H, CH$_3$), 2.52-2.63 (br s, 4H, Mor-H), 2.72 (br s, 2H, OCH$_2$CH$_2$N), 3.54-3.68 (m, 4H, Mor-H), 4.24 (m, 2H, OCH$_2$CH$_2$N), 6.85-6.87 (m, 2H, ArH), 7.21 (dd, 1H, J=9.4, 2.6 Hz, 6-H), 7.37 (d, 1H, J=2.6 Hz, 8-H), 7.50-7.52 (m, 2H, ArH), 8.12 (d, 1H, J=9.4 Hz, 5-H), 8.24 (s, 1H, 2-H), 9.15 (br s, 1H, NH). $^{13}$C NMR (100 MHz, CDCl$_3$): 12.26, 53.42 (2C), 55.58, 56.78, 65.84 (2C), 71.26, 106.73, 107.60, 109.94, 115.70 (2C), 116.68, 117.27, 124.85, 126.88 (2C), 127.55, 140.65, 141.16, 147.13, 148.04, 153.89, 160.83, 161.34. Anal. calc. for C$_{26}$H$_{27}$ClN$_4$O$_4$.2.0 H$_2$O: C, 58.81; H, 5.88; N, 10.55. found: C, 58.55; H, 6.15; N, 10.36. HRMS (ESI): calc. for C$_{26}$H$_{28}$ClN$_4$O$_4$ [M+H]$^+$: 495.1799. found: 495.1801.

Synthesis Ex. 32

(E)-1-(4-(3-Chloro-7-methoxyfuro[2,3-b]quinolin-4-ylamino)phenyl)ethanone O-4-morpholinobutyl oxime (Compound 16h)

The title compound 16h was synthesized substantially according to the procedures as set forth in the above Synthesis Example 25, except that 4-morpholinobutoxyamine.HCl was used in place of 2-aminoethoxyamine.HCl. The title compound 16h as an orange solid (98% yield) was obtained.
Detected Properties of the Title Compound:
M.p.: 124-126° C. IR (KBr): 3142, 1614, 1585, 1515. UV (MeOH): 374 (4.06), 344 (4.06), 246 (4.48), 206 (4.51). $^1$H NMR (400 MHz, CDCl$_3$): 1.54-1.78 (m, 4H, OCH$_2$(CH$_2$)$_2$CH$_2$N), 2.20 (s, 3H, CH$_3$), 2.33-2.46 (m, 6H, OCH$_2$(CH$_2$)$_2$CH$_2$N, Mor-H), 3.72-3.74 (m, 4H, Mor-H), 3.95 (s, 3H, OCH$_3$), 4.19 (t, 2H, J=6.4 Hz, OCH$_2$(CH$_2$)$_2$CH$_2$N), 6.86-6.89 (m, 2H, ArH), 6.96 (dd, 1H, J=9.4, 2.6 Hz, 6-H), 7.12 (br s, 1H, NH), 7.36 (d, 1H, J=2.6 Hz, 8-H), 7.54-7.56 (m, 2H, ArH), 7.61 (s, 1H, 2-H), 7.70 (d, 1H, J=9.4 Hz, 5-H). $^{13}$C NMR (100 MHz, CDCl$_3$): 12.54, 23.02, 27.16, 53.65 (2C), 55.51, 58.81, 66.88 (2C), 73.82, 106.11, 106.86, 110.11, 114.78, 117.18, 118.16 (2C), 125.65, 127.06 (2C), 130.95, 139.39, 141.66, 144.43, 149.04, 153.72, 161.00, 161.38. Anal. calc. for $C_{28}H_{31}ClN_4O_4 \cdot 0.7\ H_2O$: C, 62.78; H, 6.10; N, 10.46. found: C, 62.66; H, 6.40; N, 10.51. HRMS (ESI): calc. for $C_{28}H_{32}ClN_4O_4$ [M+H]$^+$: 523.2112. found: 523.2115.

Pharmacological Examples

In order to determine the biological activities of the compounds according to this invention, the following analyses were performed.
Experimental Materials:
1. Cell lines used in the following examples and sources thereof are shown in Table 2.

TABLE 2

Cell lines used in pharmacological examples and sources thereof.

| Cell line | Source | Accession No. |
|---|---|---|
| MCF-7 (breast cancer cell) | BCRC | 60436 |
| AGS (human stomach adenocarcinoma cell) | BCRC | 60102 |
| PC-3 (human prostate cancer cell) | BCRC | 60122 |
| HeLa (human cervical epithelioid carcinoma cell) | BCRC | 60005 |
| CE81T (human esophageal carcinoma cell) | BCRC | 60166 |
| MRC-5 (human lung fibroblast cell) | BCRC | 60023 |
| A549 (human lung adenocarcinoma cell) | BCRC | 60074 |
| NCI-H460 (non-small cell lung carcinoma cell) | BCRC | 60373 |
| NCI-H661 (non-small cell lung carcinoma cell) | BCRC | 60125 |
| NCI-H1299 (non-small cell lung carcinoma cell) | ATCC | CRL-5803 |
| RCC 786-O (renal cell carcinoma cell) | ATCC | CRL1932 |
| SKHep-1 (hepatocellular carcinoma cell) | ATCC | HTB-52 |
| BT483 (human breast carcinoma cell) | ATCC | HTB-121 |
| SAS (human oral squamous-cell carcinoma cell) | JCRB | JCRB0260 |
| SF-268 (central nervous system carcinoma cell) | NHRI | — |
| CL1-5 (metastatic lung adenocarcinoma cell) | Academia Sinica, Academician Yang, Pan-Chyr | — |

BCRC: Biosource Collection and Research Center of Food Industry Research and Development Institute (FIRDI).
ATCC: American Type Culture Collection.
JCRB: Japan Collection of the Research Biosources.
NHRI: National Health Research Institutes in Taiwan.

2. Male CD-1 (Crl.) mice (6-8 weeks old, about 22-24 g in weight) used in the following examples were purchased from BioLasco Taiwan Co., Ltd., and Balb/C athymic nude mice (6-8 weeks old, about 20 g in weight) used in the following examples were purchased from National Laboratory Animal Center (R.O.C., Taiwan). All of the experimental animals were raised in an animal room with an independent air conditioning system, and food and water were provided ad libitum for all of the experimental animals.

Pharmacological Ex. 1

In Vitro Anticancer Assay and Determination of Solubility in Water for Compounds of this Invention A. Evaluation of Antiproliferative Activity Antiproliferative activities of the compounds of this invention were evaluated substantially according to the method as described in Tseng, C. H. et al. (2010), *J. Med. Chem.*, 53:6164-6179. Cells of the three cancer cell lines, namely, MCF7, NCI-H460, and SF-268, were respectively seeded into wells of a 96-well plate containing Dulbecco's Modified Eagle's Medium (DMEM) supplemented with 10% fetal bovine serum (FBS), 2 mM glutamine, 100 U/mL penicillin, and 100 g/mL streptomycin at a concentration of $5 \times 10^3$ cell/well, followed by cultivation at 37° C. and in the presence of 5% $CO_2$ for 24 hours. The cells were treated with the test compounds, i.e., the compounds of this invention (in dimethylsulfoxide (DMSO)), or DMSO for 48 hours.

Before and after the treatment with the test compounds or DMSO, 3-(4,5-dimethylthiazol-2-yl)-2,5-diphenyltetrazolium bromide (MTT, 2 mg/mL, 100 μL) was added to each of the cultures, followed by cultivation for 2 hours. The resultant formazan was dissolved by the addition of DMSO. Absorbance at 570 nm (OD$_{570}$) was measured using a microtiter plate reader (Dynex MRX-II). Cell growth (%) was calculated by substituting OD$_{570}$ into the following equation:

$$A = [(B'-B)/(C'-C)] \times 100 \qquad (1)$$

where
A=cell growth
B=OD$_{570}$ measured before the treatment with the respective test compound
B'=OD$_{570}$ measured after, the treatment with the respective test compound
C=OD$_{570}$ measured before the treatment with DMSO
C'=OD$_{570}$ measured after the treatment with DMSO
Furthermore, for the purpose of comparison, compounds 1, 2, 3 as described above were also subjected to the same experiments, and served as test compounds as well. The experimental results are shown in Table 3.

TABLE 3

Evaluation for antiproliferative activities of compounds according to this invention.

| | Cell growth (%) | | | | | |
| | MCF-7 | | NCI-H460 | | SF-268 | |
| Compound | 20 mg/ml | 4 mg/ml | 20 mg/ml | 4 mg/ml | 20 mg/ml | 4 mg/ml |
|---|---|---|---|---|---|---|
| 13a | −1 | 66 | −1 | 33 | −2 | 45 |
| 13b | 0 | 59 | 0 | 94 | −5 | 81 |
| 13c | −3 | 52 | −2 | 22 | −4 | 42 |
| 13d | 22 | 84 | 7 | 52 | 0 | 62 |
| 13e | 6 | 64 | 1 | 54 | −3 | 66 |
| 13f | 3 | 114 | −1 | 99 | −3 | 96 |
| 13g | 56 | 120 | 23 | 108 | 32 | 121 |
| 13h | −2 | 76 | −1 | 118 | 2 | 125 |
| 14a | −1 | 59 | −1 | 32 | −2 | 45 |
| 14b | −3 | 70 | −1 | 68 | 2 | 71 |
| 14c | 0 | 46 | 0 | 28 | −4 | 41 |
| 14d | 1 | 61 | 1 | 52 | 1 | 66 |
| 14e | −2 | 86 | −1 | 69 | −3 | 86 |
| 14f | 26 | 121 | 3 | 101 | 31 | 120 |
| 14g | 54 | 112 | 16 | 107 | 32 | 121 |
| 14h | −3 | 75 | 3 | 91 | 3 | 115 |
| 15a | 8 | 71 | 11 | 14 | 27 | 46 |
| 15b | −1 | 67 | −1 | 75 | 1 | 91 |
| 15c | 18 | 100 | 16 | 105 | 56 | 103 |

TABLE 3-continued

Evaluation for antiproliferative activities of compounds according to this invention.

| Com-pound | Cell growth (%) | | | | | |
|---|---|---|---|---|---|---|
| | MCF-7 | | NCI-H460 | | SF-268 | |
| | 20 mg/ml | 4 mg/ml | 20 mg/ml | 4 mg/ml | 20 mg/ml | 4 mg/ml |
| 15d | 2 | 59 | 5 | 82 | 3 | 90 |
| 15e | 3 | 63 | 5 | 69 | 6 | 104 |
| 15f | 2 | 77 | 9 | 84 | 44 | 106 |
| 15g | 25 | 76 | 44 | 96 | 92 | 110 |
| 15h | 75 | 83 | 21 | 89 | 44 | 110 |
| 16a | −1 | 66 | 3 | 13 | 16 | 43 |
| 16b | −2 | 51 | −1 | 74 | −1 | 102 |
| 16c | 3 | 101 | 8 | 91 | 48 | 109 |
| 16d | 1 | 66 | 4 | 66 | 1 | 103 |
| 16e | 1 | 55 | 5 | 53 | 5 | 102 |
| 16f | −1 | 56 | 3 | 67 | 48 | 112 |

TABLE 3-continued

Evaluation for antiproliferative activities of compounds according to this invention.

| Com-pound | Cell growth (%) | | | | | |
|---|---|---|---|---|---|---|
| | MCF-7 | | NCI-H460 | | SF-268 | |
| | 20 mg/ml | 4 mg/ml | 20 mg/ml | 4 mg/ml | 20 mg/ml | 4 mg/ml |
| 16g | 37 | 85 | 68 | 97 | 108 | 104 |
| 16h | 5 | 96 | 20 | 87 | 99 | 110 |
| 1 | 61 | 69 | 30 | 33 | 39 | 40 |
| 2 | 58 | 64 | 21 | 27 | 43 | 50 |
| 3 | 37 | 63 | 23 | 51 | 42 | 68 |

As shown in Table 3, considering compounds 1, 2, 3, generally, the antiproliferative activities do not apparently greatly increase when the concentrations increase. However, considering the compounds of this invention, generally, the antiproliferative activities clearly greatly increase when the concentrations increase. After taking into account the structure and the antiproliferative activity of each compound of this invention, compounds 13a, 13c, 14a, 14c, 15a, 16a were selected to determine the concentration causing 50% cell growth inhibition ($GI_{50}$), selectivity index (SI), and solubility in water thereof.

B. Determination of $GI_{50}$ and SI

Determination of $GI_{50}$ of compounds 13a, 13c, 14a, 14c, 15a, 16a was conducted substantially according to the method as described in the preceding section A entitled "Evaluation of antiproliferative activity", except that the normal cell line MRC-5 was also utilized, and that camptothecin and daunorubicin were tested instead of compounds 1, 2, 3. The concentration of the respective test compound, which can reduce absorbance by 50% (compared with DMSO), is regarded as $GI_{50}$, and can be determined via dose-response curves. Determination of $GI_{50}$ was conducted thrice for each test compound. $GI_{50}$ is expressed as mean±SD.

SI stands for selectivity index and was calculated by substituting $GI_{50}$ into the following formula:

$$D=E/F \qquad (2)$$

where
D=SI
E=$GI_{50}$ of the respective test compound for cells of the normal cell line
F=$GI_{50}$ of the respective test compound for cells of the cancer cell line The experimental results are summarized in Table 4.

TABLE 4

$GI_{50}$ (µM) and SI of compounds 13a, 13c, 14a, 14c, 15a, 16a according to this invention

| Compound | Cell line | | | | | | |
|---|---|---|---|---|---|---|---|
| | MRC-5 | MCF-7 | | NCI-H460 | | SF-268 | |
| | $GI_{50}$ | $GI_{50}$ | SI | $GI_{50}$ | SI | $GI_{50}$ | SI |
| 13a | 42.85 ± 1.05 | 9.34 ± 0.92 | 4.59 | 0.63 ± 0.03 | 68.02 | 6.26 ± 1.02 | 6.84 |
| 13c | 42.98 ± 0.86 | 11.52 ± 0.02 | 3.73 | 7.08 ± 0.67 | 6.07 | 7.53 ± 0.41 | 5.71 |
| 14a | 47.04 ± 1.21 | 31.01 ± 0.03 | 1.52 | 0.71 ± 0.02 | 66.25 | 9.14 ± 0.72 | 5.15 |
| 14c | 47.09 ± 2.27 | 9.46 ± 0.23 | 4.98 | 16.21 ± 0.36 | 2.90 | 32.53 ± 1.25 | 1.46 |
| 15a | 45.11 ± 0.31 | 36.23 ± 0.05 | 1.24 | 3.96 ± 0.14 | 11.39 | 8.15 ± 0.44 | 5.53 |
| 16a | 47.46 ± 0.38 | 36.93 ± 0.31 | 1.28 | 3.86 ± 0.13 | 12.30 | 7.48 ± 0.366 | 6.34 |
| camptothecin | 0.89 ± 0.90 | 11.12 ± 0.61 | 0.08 | 0.03 ± 0.003 | 29.67 | 0.19 ± 0.006 | 4.68 |
| daunorubicin | 0.88 ± 0.11 | 5.03 ± 0.05 | 0.17 | 0.38 ± 0.04 | 2.32 | 0.60 ± 0.02 | 1.47 |

As shown in Table 4, generally, camptothecin and daunorubicin have low $GI_{50}$ values for the cells of MCF7, NCI-H460, and SF-268. However, growth of the cells of MRC-5 (i.e., the normal cell line) is inhibited by camptothecin and daunorubicin. Compounds 13a, 13c, 14a, 14c, 15a, 16a have much less inhibition effects on growth of the MRC-5 cells compared to camptothecin and daunorubicin. Among compounds 13a, 13c, 14a, 14c, 15a, 16a, compounds 13a, 14a have the lowest two $GI_{50}$ values for NCI-H460 cells and the highest two SI values for NCI-H460 cells. Even though $GI_{50}$ values of compounds 13a, 14a for NCI-H460 cells are slightly higher than those of camptothecin and daunorubicin for NCI-H460 cells, SI values of compounds 13a, 14a for NCI-H460 cells are much higher than those of camptothecin and daunorubicin for NCI-H460 cells.

C. Determination of Solubility in Water

In order to investigate the effect of the aminoalkyl group attached to the oxime moiety upon the solubility in water regarding the compounds of this invention, compounds 13a, 13c, 14a, 14c, 15a, 16a were tested in the following experiment. The hydrochloride salt of compound 13a was also tested in the following experiment. Additionally, for the purpose of comparison, compounds 1, 2, 3 were tested in the following experiment as well.

Determination of solubility in water was conducted substantially according to the method as described in Vougogiannopoulou, K. et al. (2008), *J. Med. Chem.*, 51:6421-6431. An excess amount of the respective test compound was added into water, followed by sonication for 5 minutes. The resultant mixture was stirred at ambient temperature (25±0.1° C.)

overnight. Centrifugation at 4000 rpm and 25° C. was conducted for 5 minutes. Absorbance of the sample of the respective test compound was measured at 315-420 nm using a UV-VIS spectrophotometer (JASCO UV-Visible V570). For each test compound, a standard curve was generated by plotting concentrations of standard solutions and the corresponding absorbances. The absorbance of the sample of each test compound was then converted to solubility in water (μg/mL) using the corresponding standard curve. The experimental results are shown in Table 5.

TABLE 5

Solubility in water regarding compounds 13a, 13c, 14a, 14c, 15a, 16a according to this invention

| | Compound | | | | | | | | | |
|---|---|---|---|---|---|---|---|---|---|---|
| | 13a | Hydrochloride salt of 13a | 13c | 14a | 14c | 15a | 16a | 1 | 2 | 3 |
| Solubility in water (μg/mL) | 63 | 1049 | 58 | 25 | 36 | 16 | 17 | 6 | 10 | 8 |

As shown in Table 5, in contrast with compounds 1, 2, 3, the solubility in water regarding each of compounds 13a, 13c, 14a, 14c, 15a, 16a according to this invention is higher. In particular, compound 13a has the highest solubility in water among compounds 13a, 13c, 14a, 14c, 15a, 16a. Moreover, the solubility in water regarding compound 13a is about six times higher than that regarding compound 2, thereby indicating that introduction of an aminoethyl group to an oxime moiety is certainly able to enhance solubility in water. In addition, the solubility in water regarding the hydrochloride salt of compound 13a is about 17 times higher than that regarding compound 13a.

Based on the experimental results of section A of Pharmacological Example 1, the compounds of formula (I) according to this invention are expected to be useful in the treatment of cancer. Since the experimental results of sections B and C of Pharmacological Example 1 reveal that compounds 13a, 14a have satisfactory SI values and solubility in water, the applicants further tested the single-dose pharmacokinetics of compounds 13a, 14a so as to evaluate the potential of compounds 13a, 14a for use as an anticancer composition.

Pharmacological Ex. 2

Single-Dose Pharmacokinetic Analysis for Compounds 13a, 14a of this Invention

Single-Dose Pharmacokinetic Analysis for Compounds 13a, 14a of this Invention was Conducted by Rosetta Pharmamate Co., Ltd. (R.O.C., Taiwan).

CD-1 mice were divided into two groups. The first group of mice (n=9) were used to assess the singe-dose pharmacokinetics of the test compounds after intravenous administration, and the second group of mice (n=9) were utilized to assess the singe-dose pharmacokinetics of the test compounds after oral administration. All of the mice were fasted from 4 hours before the administration of the test compounds until 4 hours after the administration of the test compounds.

The assessment for singe-dose pharmacokinetics of the test compounds after intravenous administration was performed as follows. The first group of mice were further randomly divided into three subgroups including compound 13a group (n=3), compound 14a group (n=3), and compound 1 group (n=3). Compounds 13a, 14a, 1 (in polyethylene glycol 400/ethanol/water (30/5/65, v/v/v)) were respectively administered to the mice in compound 13a group, compound 14a group, and compound 1 group at a dose of 2 mg/kg via tail vein injection. Blood samples (0.25 mL) were collected from the mice by virtue of cardiac puncture right before the intravenous administration, and at 2 min, 5 min, 15 min, 30 min, 1 hr, 1.5 hr, 2 hr, 4 hr, 6 hr, 9 hr, 24 hr, and 27 hr after the intravenous administration.

The assessment for singe-dose pharmacokinetics of the test compounds after oral administration was conducted as follows. The second group of mice were further randomly divided into three subgroups including compound 13a group (n=3), compound 14a group (n=3), and compound 1 group (n=3). Compounds 13a, 14a, 1 (in 0.5% methylcellulose) were respectively administered to the mice in compound 13a group, compound 14a group, and compound 1 group at a dose of 20 mg/kg via tube feeding. Blood samples (0.25 mL) were collected from the mice by virtue of cardiac puncture right before the oral administration, and at 15 min, 30 min, 1 hr, 1.5 hr, 2 hr, 4 hr, 6 hr, 9 hr, 24 hr, and 27 hr after the oral administration.

Each of the blood samples was placed in a 0.5 mL Microtainer® tube containing anticoagulant EDTA-$K_2$, followed by mixing evenly. Centrifugation at 7000 g and 4° C. was conducted for 5 minutes. Plasma was collected and was mixed uniformly with a proper amount of acetonitrile, followed by centrifugation. The resultant supernatant was acquired, and was injected into a reversed-phase Biosil ODS column so as to determine the concentration of the respective test compound in plasma (i.e., the plasma concentration of the respective test compound) using a LC-MS/MS system (Waters 2795 LC and Micromass Quattro Ultima). The singe-dose pharmacokinetic parameters of the respective test compound were calculated from the obtained concentration of the respective test compound in plasma (i.e., the obtained plasma concentration of the respective compound) at different time points using WinNonlin Standard Program (version 3.1, Pharsight Corp.)

Figure 2:
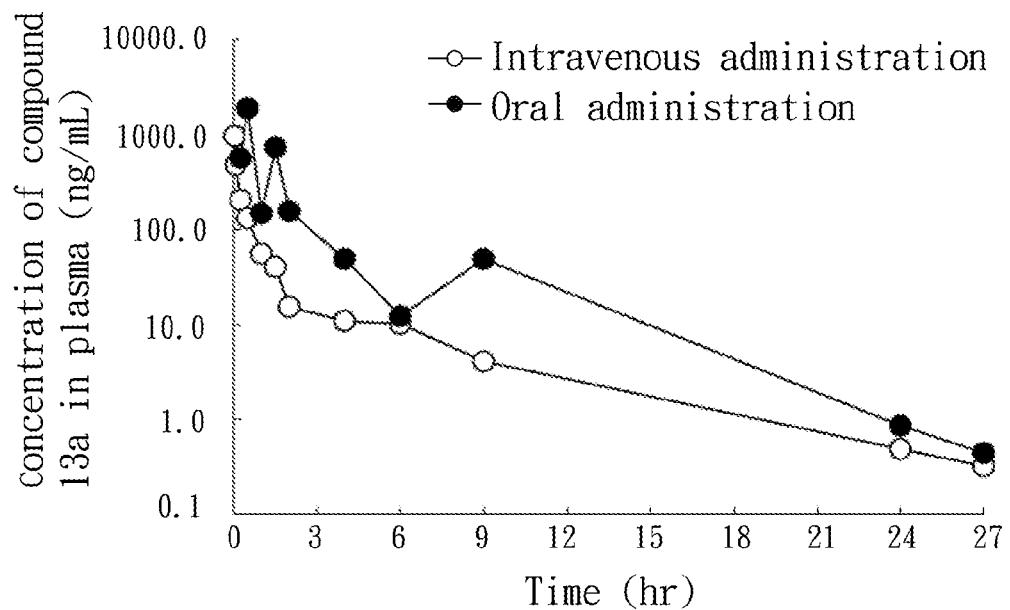
FIG. 2 shows the concentration of compound 13a in plasma at different time points after the intravenous administration or the oral administration of compound 13a to CD-1 mice.
Figure 3:
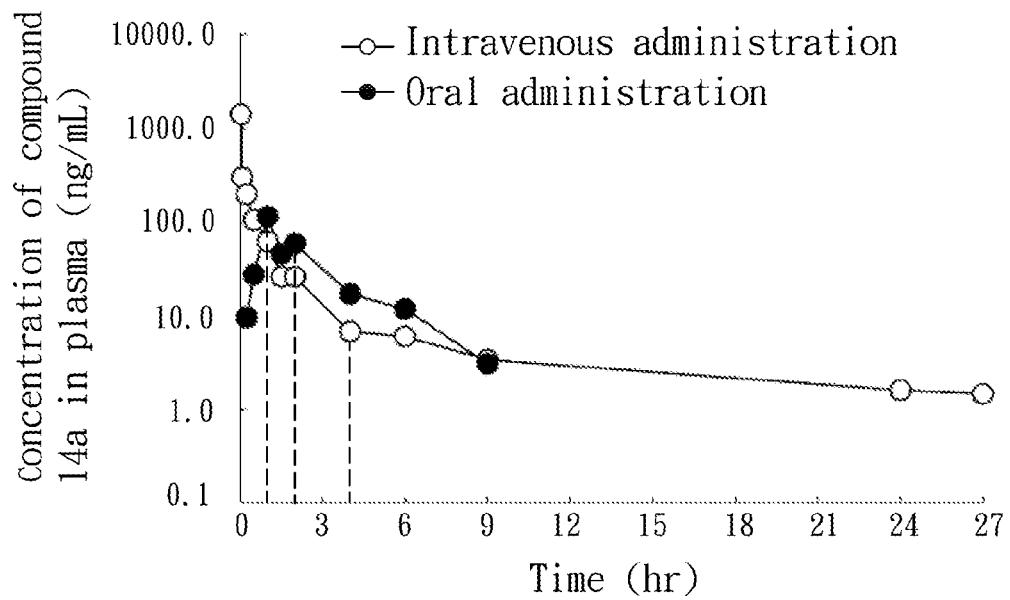
FIG. 3 shows the concentration of compound 14a in plasma at different time points after the intravenous administration or the oral administration of compound 14a to CD-1 mice.

Results:

FIG. 1 shows the concentration of compound 1 in plasma at different time points after the intravenous administration or the oral administration of compound 1 to the CD-1 mice. FIG. 2 shows the concentration of compound 13a in plasma at different time points after the intravenous administration or the oral administration of compound 13a to the CD-1 mice. FIG. 3 shows the concentration of compound 14a in plasma at different time points after the intravenous administration or the oral administration of compound 14a to the CD-1 mice.

As shown in FIG. 1, the intravenously administered compound 1 was unable to be detected in plasma after 1.5 hr, and the orally administered compound 1 was incapable of being detected in plasma after 6 hr.

As shown in FIG. 2, the concentration of the intravenously administered compound 13a in plasma rapidly decreased with time until 2 hr, and slowly decreased with time from 2 hr to 27 hr. The plot regarding the concentration of the orally administered compound 13a in plasma vs. time has the highest peak at 0.5 hr ($T_{max}$=0.5 hr) and the second-highest and the third-highest peaks respectively at 1.5 hr and 9 hr, and the concentration of the orally administered compound 13a in plasma is generally higher than that of the intravenously administered compound 13a in plasma from 0 to 27 hr. The aforesaid experimental results reveal that compound 13a can be rapidly absorbed if the same is orally administered to a mouse, and that several absorption sites for compound 13a might exist in a mouse.

As shown in FIG. 3, the concentration of the intravenously administered compound 14a in plasma rapidly decreased with time until 4 hr, and slowly decreased with time from 4 hr to 27 hr. The plot regarding the concentration of the orally administered compound 14a in plasma vs. time has the highest peak at 1.0 hr ($T_{max}$=1.0 hr) and the second-highest peak at 2 hr, and the concentration of the orally administered compound 14a in plasma slowly decreased with time from 2 hr to 9 hr. The orally administered compound 14a was unable to be detected after 9 hr.

The calculated singe-dose pharmacokinetic parameters of the test compounds are summarized in Table 6.

TABLE 6

Singe-dose pharmacokinetic parameters of compounds 1, 13a, 14a

| | Singe-dose pharmacokinetic parameter | Compd. 1 | Compd. 13a | Compd. 14a |
|---|---|---|---|---|
| Intravenous administration | $C_{max}$(ng/mL)$^a$ | 3064 | 1488.4 | 3601 |
| | $AUC_{(0-inf)}$ (ng × hr/mL) | 211 | 362.6 | 409.8 |
| | MRT (hr) | 0.1 | 2.5 | 6.1 |
| | CL (mL/(min × kg)) | 158 | 91.9 | 81.3 |
| | $V_{ss}$ (L/kg) | 1.2 | 13.5 | 30.0 |
| | $V_z$ (L/kg) | 4.1 | 38.8 | 103.8 |
| | $t_{1/2}$ (hr) | 0.3$^b$ | 4.9$^d$ | 14.7$^d$ |
| Oral administration | $C_{max}$(ng/mL) | 21 | 1905.0 | 114.3 |
| | $AUC_{(0-inf)}$ (ng × hr/mL) | 45 | 2071.6 | 242.6 |
| | $T_{max}$(hr) | 0.3 | 0.5 | 1.0 |
| | MRT (hr) | 2.7 | 3.0 | 2.8 |
| | $t_{1/2}$ (hr) | 2.0$^c$ | 3.4$^e$ | 1.7$^f$ |
| | Bioavailability (%) | 2.1 | 57.1 | 5.9 |

$^a$$C_{max}$ was determined from the extrapolated plasma concentration of the test compound at 0 hr.
$^b$$t_{1/2}$ was determined from the plasma concentration of the test compound at time points ranging from 0.5 hr to 1.5 hr.
$^c$$t_{1/2}$ was determined from the plasma concentration of the test compound at time points ranging from 2 hr to 6 hr.
$^d$$t_{1/2}$ was determined from the plasma concentration of the test compound at time points ranging from 9 hr to 27 hr.
$^e$$t_{1/2}$ was determined from the plasma concentration of the test compound at time points ranging from 2 hr to 24 hr.
$^f$$t_{1/2}$ was determined from the plasma concentration of the test compound at time points ranging from 2 hr to 9 hr.

As shown in Table 6, among the orally administered compounds 1, 13a, 14a, the orally administered compound 13a has the longest half-life ($t_{1/2}$), which is 3.4 hours, and the highest bioavailability (57.1%). Furthermore, $C_{max}$ and AUC of the orally administered compound 13a are respectively much higher than those of the orally administered compounds 1, 14a.

Even though compounds 13a, 14a of this invention have similar in vitro antiproliferative activities and SI, compound 13a has better bioavailability and longer half-life compared to compound 14a, and can be absorbed by a living subject in a manner like that of sustain-released drugs. Consequently, in contrast with compound 14a, compound 13a is deemed more suitable to be developed into an oral anticancer drug.

Pharmacological Ex. 3

Evaluation for Preferential Antiproliferative Activity of Compound 13a According to this Invention In order to examine whether compound 13a of this invention has preferential antiproliferative activities against different types of cancer cells, the preferential antiproliferative activity of compound 13a was evaluated substantially according to the method as described in section B, entitled "Determination of $GI_{50}$ and SI", of Pharmacological Example 1, using the following cancer cell lines: RCC 786-0, AGS, PC-3, BT483, HeLa, SAS, SKHep, CE81T, A549, NCI-H1299, NCI-H460, NCI-H611, and CL1-5. The experimental results are summarized in Table 7.

TABLE 7

Evaluation for preferential antiproliferative activity of compound 13a

| Cell line | $GI_{50}$ (µM) | SI |
|---|---|---|
| RCC 786-O | 24.0 ± 2.0 | 1.77 |
| AGS | 13.77 ± 0.04 | 3.09 |
| PC-3 | 11.85 ± 0.49 | 3.62 |
| BT483 | 10.16 ± 0.90 | 4.22 |
| HeLa | 8.31 ± 0.60 | 5.16 |
| SAS | 15.50 ± 2.60 | 2.76 |
| SKHep | 13.13 ± 3.75 | 3.26 |
| CE81T | 16.95 ± 1.88 | 2.53 |
| A549 | 6.58 ± 2.99 | 6.51 |
| NCI-H1299 | 3.08 ± 1.12 | 13.91 |
| NCI-H460 | 0.63 ± 0.03 | 68.02 |
| NCI-H611 | 0.98 ± 0.27 | 43.72 |
| CL1-5 | 5.18 $^a$ | 8.27 |
| MRC-5 | 42.85 ± 1.05 | — |

$^a$ The result based on a single trial.

As shown in Table 7, among all the cancer cell lines used in this example, compound 13a has the highest SI value for NCI-H460 and the second highest SI value for NCI-H611. The SI values of compound 13a for A549, NCI-H1299, and CL1-5 are acceptable. The aforementioned experimental results show that compound 13a of this invention has a preferential antiproliferative activity against lung cancer.

Pharmacological Ex. 4

Evaluation for Effect of Compound 13a According to this Invention Upon In Vivo Inhibition of Lung Cancer Cells In vivo animal model tests employing nude mice were performed so as to investigate whether compound 13a according to this invention has in vivo anticancer activity against lung cancer cells.

$10^6$ NCI-H460 cells were mixed evenly with a proper amount of Matrigel (BD Biosciences). The resultant mixture was injected subcutaneously into each of the nude mice on a dorsal flank close to an upper portion of a hind leg. When the nude mice had a tumor larger than or equal to 5 mm$^3$, the same could be used for the following experiment.

The nude mice bearing a tumor were randomly divided into two groups. The first group (n=14) of the nude mice was used to evaluate the effect of compound 13a after intraperitoneal injection, and was further divided into three subgroups including 10 mg/kg group (n=4), 20 mg/kg group (n=6), and a control group (n=4). Compound 13a (in DMSO/Tween 80/PBS (1/1/8, v/v/v)) was administered to the nude mice in 10 mg/kg group and 20 mg/kg group respectively at a dose of 10 mg/kg and a dose of 20 mg/kg via intraperitoneal injection, and 5% dextrose was administered to the nude mice in the control group at the same dosing volume as compound 13a via intraperitoneal injection.

The second group (n=28) of the nude mice was used to evaluate the effect of compound 13a after oral administration, and was further divided into three subgroups including 60 mg/kg group (n=10), 120 mg/kg group (n=10), and a control group (n=8). Compound 13a (in a normal saline solution containing 1% DMSO, 1.4% Tween 80, and 1% sodium carboxymethyl cellulose (Sigma), and serving as a vehicle) was administered to the nude mice in 60 mg/kg group and 120 mg/kg group respectively at a dose of 60 mg/kg and a dose of 120 mg/kg via tube feeding (0.22-0.26 mL of the mixture of compound 13a and the vehicle/nude mouse), and the vehicle was administered to the mice in the control group at a dose of 10 mL/kg via tube feeding.

Administration was conducted once daily for 6 consecutive days. For the first group of the nude mice, the size of the tumor on the dorsal flank was measured with calipers every 9 days for 100 consecutive days. For the second group of the nude mice, the survival rate was calculated every 10 days starting on Day 1 (i.e., the day of the second administration) for 80 consecutive days, and the size of the tumor on the dorsal flank was measured with the calipers every 3 days for 32 consecutive days.

Figure 4:
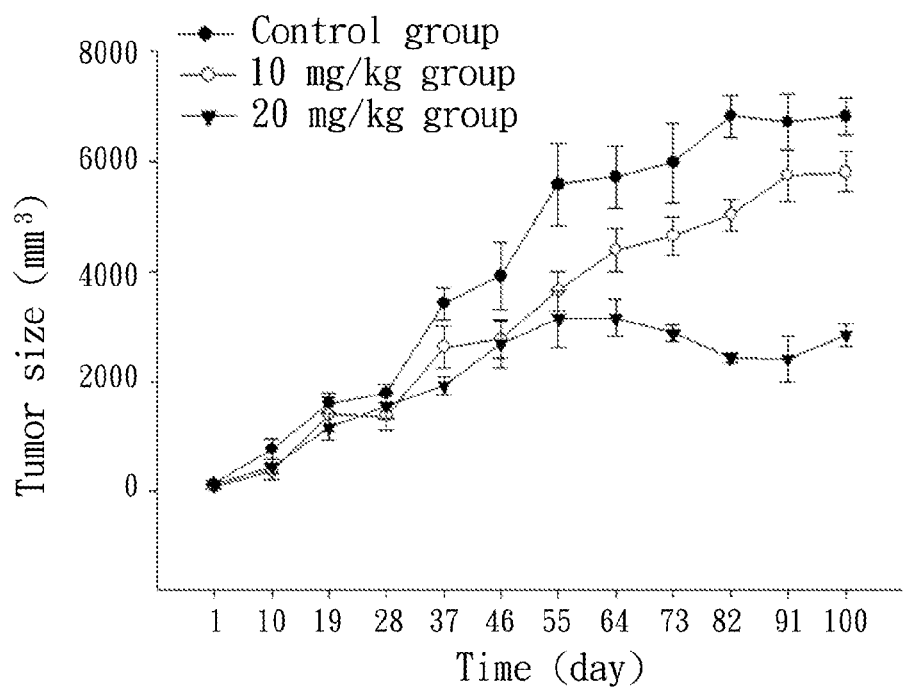
FIG. 4 shows the size of the tumor of nude mice treated with compound 13a of this invention via intraperitoneal injection at different time points.
Figure 5:
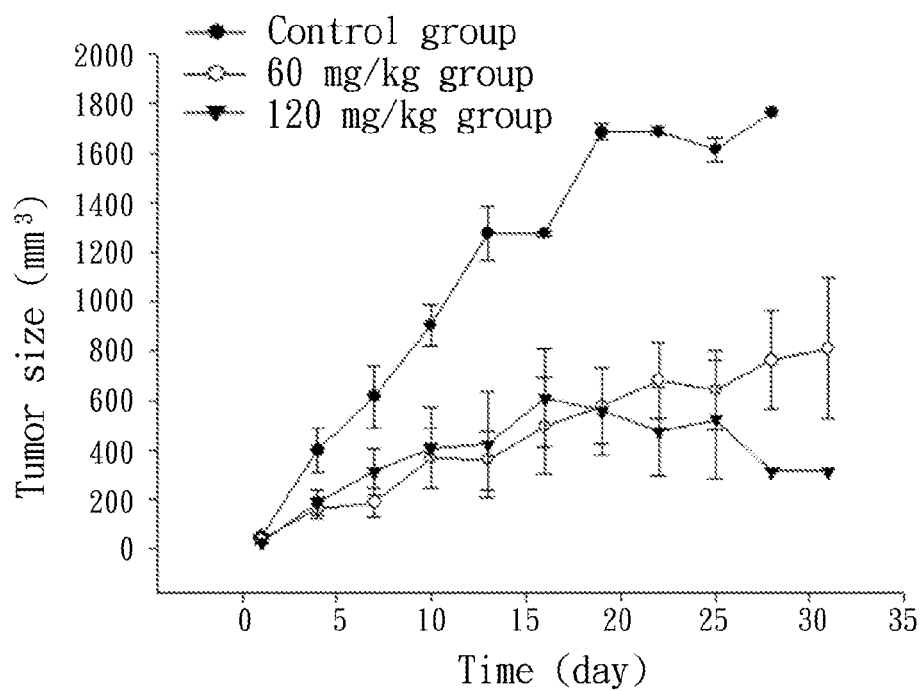
FIG. 5 shows the size of the tumor of nude mice treated with compound 13a of this invention via oral administration at different time points.

Results:

FIG. 4 shows the size of the tumor of the nude mice treated with compound 13a of this invention via intraperitoneal injection at different time points. FIG. 5 shows the size of the tumor of the nude mice treated with compound 13a of this invention via oral administration at different time points. As shown in FIGS. 4 and 5, the tumor of the nude mice in the control groups belonging to the first and second groups grew more rapidly with time, but the tumor of the nude mice treated with compound 13a generally grew more slowly with time. In particular, the tumor of the nude mice treated with compound 13a via the oral administration of the dose of 120 mg/kg diminished in size after Day 16.

Figure 6:
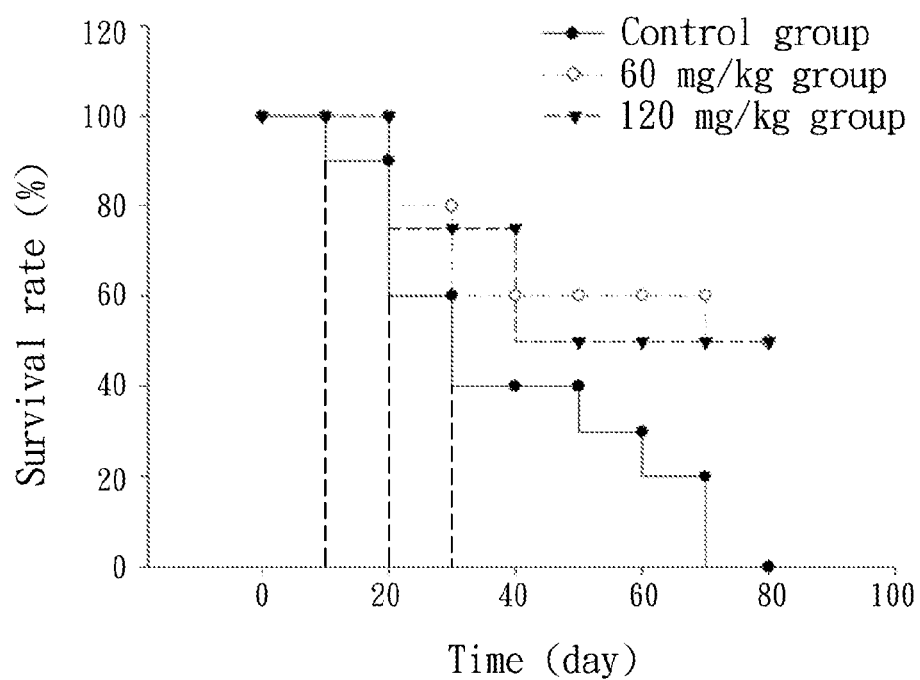
FIG. 6 shows the survival rate of the nude mice treated with compound 13a of this invention via oral administration at different time points.

FIG. 6 shows the survival rate of the nude mice treated with compound 13a of this invention via oral administration at different time points. As shown in FIG. 6, the nude mice in the control group of the second group were all dead on Day 80, but 50% of the nude mice in each of 60 mg/kg group and 120 mg/kg group still survived on Day 80.

The aforesaid experimental results reveal that: compound 13a of this invention is able to effectively inhibit growth of a tumor of a living subject, and is hence capable of enhancing the survival rate of the living subject. Thus, compound 13a of this invention is very likely to be developed into a potent anticancer drug.

All patents and literature references cited in the present specification as well as the references described therein, are hereby incorporated by reference in their entirety. In case of conflict, the present description, including definitions, will prevail.

While the invention has been described with reference to the above specific embodiments, it is apparent that numerous modifications and variations can be made without departing from the scope and spirit of this invention. It is therefore intended that this invention be limited only as indicated by the appended claims.

We claim:

1. A compound of formula (I):

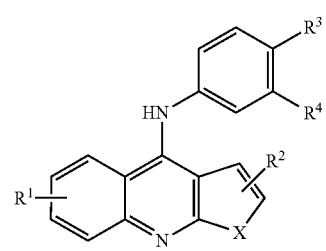

or a pharmaceutically acceptable salt thereof,
wherein:
X represents S, O, or NH;
$R^1$ and $R^2$, which may be the same or different, independently represent: H, halogen, a $C_1$-$C_4$ alkyl group, a hydroxyl group, a $C_1$-$C_4$ alkoxy group, a nitro group, or an amino group; and
one of $R^3$ and $R^4$ is H, and the other is

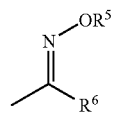

wherein $R^5$ is a $C_2$-$C_8$ aminoalkyl group, and $R^6$ represents H or a $C_1$-$C_4$ alkyl group.

2. The compound of claim 1, which has formula (II):

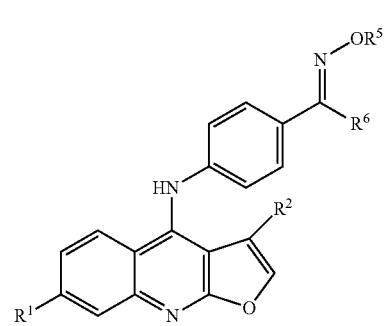

wherein:
$R^1$ represents H or a $C_1$-$C_4$ alkoxy group;
$R^2$ represents H or halogen;
$R^5$ is a $C_2$-$C_8$ aminoalkyl group; and
$R^6$ is a $C_1$-$C_4$ alkyl group.

3. The compound of claim 2, wherein $R^5$ is:

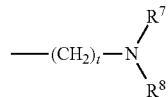

wherein:
$R^7$ and $R^8$, which may be the same or different, independently represent H or an alkyl group; and t is an integer from 2 to 4.

4. The compound of claim 2, wherein $R^5$ is:

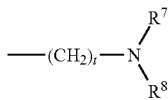

wherein:
$R^7$ and $R^8$ together with the nitrogen atom to which $R^7$ and $R^8$ are attached form a 5- to 6-membered heterocyclic ring; and t is an integer from 2 to 4.

5. The compound of claim 4, wherein $R^7$ and $R^8$ together with the nitrogen atom to which $R^7$ and $R^8$ are attached form a 6-membered heterocyclic ring that has an oxygen atom.

6. The compound of claim 2, wherein $R^5$ is selected from the group consisting of:

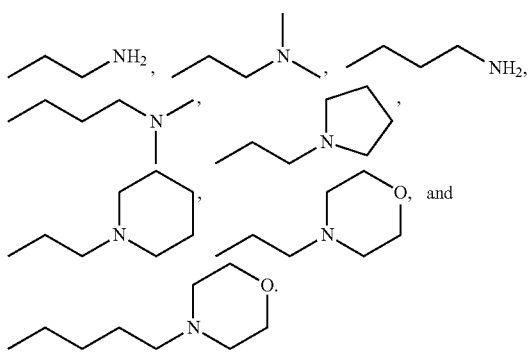

7. The compound of claim 2, which is selected from the group consisting of:
- (E)-1-(4-(furo[2,3-b]quinolin-4-ylamino)phenyl)ethanone O-2-aminoethyl oxime;
- (E)-1-(4-(furo[2,3-b]quinolin-4-ylamino)phenyl)ethanone O-2-(dimethylamino)ethyl oxime;
- (E)-1-(4-(furo[2,3-b]quinolin-4-ylamino)phenyl)ethanone O-3-aminopropyl oxime;
- (E)-1-(4-(furo[2,3-b]quinolin-4-ylamino)phenyl)ethanone O-3-(dimethylamino)propyl oxime;
- (E)-1-(4-(furo[2,3-b]quinolin-4-ylamino)phenyl)ethanone O-2-(pyrrolidin-1-yl)ethyl oxime;
- (E)-1-(4-(furo[2,3-b]quinolin-4-ylamino)phenyl)ethanone O-2-(piperidin-1-yl)ethyl oxime;
- (E)-1-(4-(furo[2,3-b]quinolin-4-ylamino)phenyl)ethanone O-2-morpholinoethyl oxime;
- (E)-1-(4-(furo[2,3-b]quinolin-4-ylamino)phenyl)ethanone O-4-morpholinobutyl oxime;
- (E)-1-(4-(3-chlorofuro[2,3-b]quinolin-4-ylamino)phenyl)ethanone O-2-aminoethyl oxime;
- (E)-1-(4-(3-chlorofuro[2,3-b]quinolin-4-ylamino)phenyl)ethanone O-2-(dimethylamino)ethyl oxime;
- (E)-1-(4-(3-chlorofuro[2,3-b]quinolin-4-ylamino)phenyl)ethanone O-3-aminopropyl oxime;
- (E)-1-(4-(3-chlorofuro[2,3-b]quinolin-4-ylamino)phenyl)ethanone O-3-(dimethylamino)propyl oxime;
- (E)-1-(4-(3-chlorofuro[2,3-b]quinolin-4-ylamino)phenyl)ethanone O-2-(pyrrolidin-1-yl)ethyl oxime;
- (E)-1-(4-(3-chlorofuro[2,3-b]quinolin-4-ylamino)phenyl)ethanone O-2-(piperidin-1-yl)ethyl oxime;
- (E)-1-(4-(3-chlorofuro[2,3-b]quinolin-4-ylamino)phenyl)ethanone O-2-morpholinoethyl oxime;
- (E)-1-(4-(3-chlorofuro[2,3-b]quinolin-4-ylamino)phenyl)ethanone O-4-morpholinobutyl oxime;
- (E)-1-(4-(7-methoxyfuro[2,3-b]quinolin-4-ylamino)phenyl)ethanone O-2-aminoethyl oxime;
- (E)-1-(4-(7-methoxyfuro[2,3-b]quinolin-4-ylamino)phenyl)ethanone O-2-(dimethylamino)ethyl oxime;
- (E)-1-(4-(7-methoxyfuro[2,3-b]quinolin-4-ylamino)phenyl)ethanone O-3-aminopropyl oxime;
- (E)-1-(4-(7-methoxyfuro[2,3-b]quinolin-4-ylamino)phenyl)ethanone O-3-(dimethylamino)propyl oxime;
- (E)-1-(4-(7-methoxyfuro[2,3-b]quinolin-4-ylamino)phenyl)ethanone O-2-(pyrrolidin-1-yl)ethyl oxime;
- (E)-1-(4-(7-methoxyfuro[2,3-b]quinolin-4-ylamino)phenyl)ethanone O-2-(piperidin-1-yl)ethyl oxime;
- (E)-1-(4-(7-methoxyfuro[2,3-b]quinolin-4-ylamino)phenyl)ethanone O-2-morpholinoethyl oxime;
- (E)-1-(4-(7-methoxyfuro[2,3-b]quinolin-4-ylamino)phenyl)ethanone O-4-morpholinobutyl oxime;
- (E)-1-(4-(3-chloro-7-methoxyfuro[2,3-b]quinolin-4-ylamino)phenyl) ethanone O-2-aminoethyl oxime;
- (E)-1-(4-(3-chloro-7-methoxyfuro[2,3-b]quinolin-4-ylamino)phenyl) ethanone O-2-(dimethylamino) ethyl oxime;
- (E)-1-(4-(3-chloro-7-methoxyfuro[2,3-b]quinolin-4-ylamino)phenyl) ethanone O-3-aminopropyl oxime;
- (E)-1-(4-(3-chloro-7-methoxyfuro[2,3-b]quinolin-4-ylamino)phenyl) ethanone O-3-(dimethylamino) propyl oxime;
- (E)-1-(4-(3-chloro-7-methoxyfuro[2,3-b]quinolin-4-ylamino)phenyl) ethanone O-2-(pyrrolidin-1-yl)ethyl oxime;
- (E)-1-(4-(3-chloro-7-methoxyfuro[2,3-b]quinolin-4-ylamino)phenyl) ethanone O-2-(piperidin-1-yl)ethyl oxime;
- (E)-1-(4-(3-chloro-7-methoxyfuro[2,3-b]quinolin-4-ylamino)phenyl) ethanone O-2-morpholinoethyl oxime;
- (E)-1-(4-(3-chloro-7-methoxyfuro[2,3-b]quinolin-4-ylamino)phenyl) ethanone O-4-morpholinobutyl oxime; and salts thereof.

8. The compound of claim 7, which is a hydrochloride salt of (E)-1-(4-(furo[2,3-b]quinolin-4-ylamino)phenyl)ethanone O-2-aminoethyl oxime.

9. A pharmaceutical composition, comprising a compound of formula (I) as claimed in claim 1 or a pharmaceutically acceptable salt thereof.

10. The pharmaceutical composition of claim 9, wherein the compound of formula (I) as claimed in claim 1 is selected from the group consisting of:
- (E)-1-(4-(furo[2,3-b]quinolin-4-ylamino)phenyl)ethanone O-2-aminoethyl oxime;
- (E)-1-(4-(furo[2,3-b]quinolin-4-ylamino)phenyl)ethanone O-2-(dimethylamino)ethyl oxime;
- (E)-1-(4-(furo[2,3-b]quinolin-4-ylamino)phenyl)ethanone O-3-aminopropyl oxime;
- (E)-1-(4-(furo[2,3-b]quinolin-4-ylamino)phenyl)ethanone O-3-(dimethylamino)propyl oxime;
- (E)-1-(4-(furo[2,3-b]quinolin-4-ylamino)phenyl)ethanone O-2-(pyrrolidin-1-yl)ethyl oxime;
- (E)-1-(4-(furo[2,3-b]quinolin-4-ylamino)phenyl)ethanone O-2-(piperidin-1-yl)ethyl oxime;
- (E)-1-(4-(furo[2,3-b]quinolin-4-ylamino)phenyl)ethanone O-2-morpholinoethyl oxime;
- (E)-1-(4-(furo[2,3-b]quinolin-4-ylamino)phenyl)ethanone O-4-morpholinobutyl oxime;

(E)-1-(4-(3-chlorofuro[2,3-b]quinolin-4-ylamino)phenyl) ethanone O-2-aminoethyl oxime;
(E)-1-(4-(3-chlorofuro[2,3-b]quinolin-4-ylamino)phenyl) ethanone O-2-(dimethylamino)ethyl oxime;
(E)-1-(4-(3-chlorofuro[2,3-b]quinolin-4-ylamino)phenyl) ethanone O-3-aminopropyl oxime;
(E)-1-(4-(3-chlorofuro[2,3-b]quinolin-4-ylamino)phenyl) ethanone O-3-(dimethylamino)propyl oxime;
(E)-1-(4-(3-chlorofuro[2,3-b]quinolin-4-ylamino)phenyl) ethanone O-2-(pyrrolidin-1-yl)ethyl oxime;
(E)-1-(4-(3-chlorofuro[2,3-b]quinolin-4-ylamino)phenyl) ethanone O-2-(piperidin-1-yl)ethyl oxime;
(E)-1-(4-(3-chlorofuro[2,3-b]quinolin-4-ylamino)phenyl) ethanone O-2-morpholinoethyl oxime;
(E)-1-(4-(3-chlorofuro[2,3-b]quinolin-4-ylamino)phenyl) ethanone O-4-morpholinobutyl oxime;
(E)-1-(4-(7-methoxyfuro[2,3-b]quinolin-4-ylamino)phenyl)ethanone O-2-aminoethyl oxime;
(E)-1-(4-(7-methoxyfuro[2,3-b]quinolin-4-ylamino)phenyl)ethanone O-2-(dimethylamino)ethyl oxime;
(E)-1-(4-(7-methoxyfuro[2,3-b]quinolin-4-ylamino)phenyl)ethanone O-3-aminopropyl oxime;
(E)-1-(4-(7-methoxyfuro[2,3-b]quinolin-4-ylamino)phenyl)ethanone O-3-(dimethylamino)propyl oxime;
(E)-1-(4-(7-methoxyfuro[2,3-b]quinolin-4-ylamino)phenyl)ethanone O-2-(pyrrolidin-1-yl)ethyl oxime;
(E)-1-(4-(7-methoxyfuro[2,3-b]quinolin-4-ylamino)phenyl)ethanone O-2-(piperidin-1-yl)ethyl oxime;
(E)-1-(4-(7-methoxyfuro[2,3-b]quinolin-4-ylamino)phenyl)ethanone O-2-morpholinoethyl oxime;
(E)-1-(4-(7-methoxyfuro[2,3-b]quinolin-4-ylamino)phenyl)ethanone O-4-morpholinobutyl oxime;
(E)-1-(4-(3-chloro-7-methoxyfuro[2,3-b]quinolin-4-ylamino)phenyl) ethanone O-2-aminoethyl oxime;
(E)-1-(4-(3-chloro-7-methoxyfuro[2,3-b]quinolin-4-ylamino)phenyl) ethanone O-2-(dimethylamino) ethyl oxime;
(E)-1-(4-(3-chloro-7-methoxyfuro[2,3-b]quinolin-4-ylamino)phenyl) ethanone O-3-aminopropyl oxime;
(E)-1-(4-(3-chloro-7-methoxyfuro[2,3-b]quinolin-4-ylamino)phenyl) ethanone O-3-(dimethylamino) propyl oxime;
(E)-1-(4-(3-chloro-7-methoxyfuro[2,3-b]quinolin-4-ylamino)phenyl) ethanone O-2-(pyrrolidin-1-yl)ethyl oxime;
(E)-1-(4-(3-chloro-7-methoxyfuro[2,3-b]quinolin-4-ylamino)phenyl) ethanone O-2-(piperidin-1-yl)ethyl oxime;
(E)-1-(4-(3-chloro-7-methoxyfuro[2,3-b]quinolin-4-ylamino)phenyl) ethanone O-2-morpholinoethyl oxime;
(E)-1-(4-(3-chloro-7-methoxyfuro[2,3-b]quinolin-4-ylamino)phenyl) ethanone O-4-morpholinobutyl oxime; and
salts thereof.

11. The pharmaceutical composition of claim 10, wherein the compound of formula (I) claimed in claim 1 is (E)-1-(4-(furo[2,3-b]quinolin-4-ylamino)phenyl)ethanone O-2-aminoethyl oxime.

12. The pharmaceutical composition of claim 10, wherein the compound of formula (I) claimed in claim 1 is a hydrochloride salt of (E)-1-(4-(furo[2,3-b]quinolin-4-ylamino)phenyl)ethanone O-2-aminoethyl oxime.

\* \* \* \* \*